United States Patent [19]

Nichol et al.

[11] Patent Number: 5,945,277
[45] Date of Patent: Aug. 31, 1999

[54] STRAIN OF HANTAVIRUS NUCLEOTIDE SEQUENCES THEREOF RELATED PROBES, PRIMERS AND VECTORS, AND METHODS FOR DETECTION

[75] Inventors: Stuart T. Nichol; Christina F. Spiropoulou, both of Atlanta; Thomas G. Ksiazek; Pierre E. Rollin, both of Lilburn, all of Ga.

[73] Assignee: The United States of America as represented by the Department of Health and Human Services, Washington, D.C.

[21] Appl. No.: 08/657,641

[22] Filed: May 30, 1996

Related U.S. Application Data

[63] Continuation of application No. 08/133,591, Oct. 7, 1993, abandoned, which is a continuation-in-part of application No. 08/084,724, Jun. 24, 1993, abandoned.

[51] Int. Cl.⁶ .............................. C12Q 1/70; C12Q 1/68; C12P 19/34; C07H 21/04
[52] U.S. Cl. .................. 435/5; 435/6; 435/91.1; 435/91.51; 536/23.72; 536/24.33
[58] Field of Search ................................... 435/5, 6, 91.1, 435/91.2, 320.1, 243, 183, 91.51; 536/23.1, 23.72, 24.32, 24.33; 935/8, 77, 78

[56] References Cited

U.S. PATENT DOCUMENTS

| 5,183,658 | 2/1993 | Lee et al. ................................. 424/89 |
| 5,298,423 | 3/1994 | Dalrymple et al. .................. 435/320.1 |

OTHER PUBLICATIONS

New England Bio Labs 1988–1989 Catalog, pp. 54, and 62–64.
*Nucleic Acids Research,* vol. 17, No. 16, Sommer and Tautz, p. 6749, 1989.
Sequence Comparison, pp. 25–26, #6.
Antic et al., "Comparison of the deduced gene products of the L, M, and S genome segments of hantaviruses," *Virus Res.* 24:35–46 (1992).
CDC, "Outbreak of acute illness—Southwestern United States, 1993," *Morbidity and Mortality Weekly Report* 42:421–424 (Jun. 11, 1993).
CDC, "Update: Outbreak of acute illness—Southwestern United States, 1993," *Morbidity and Mortality Weekly Report* 42:441–443 (Jun. 18, 1993).
CDC, "Update: Outbreak of acute illness—Southwestern United States, 1993," *Morbidity and Mortality Weekly Report* 42:477–479 (Jun. 25, 1993).
CDC, "Update: Outbreak of acute illness—Southwestern United States, 1993," *Morbidity and Mortality Weekly Report* 42:495–496 (Jul. 2, 1993).
CDC, "Update: Outbreak of acute illness—Southwestern United States, 1993," *Morbidity and Mortality Weekly Report* 42:570–571 (Jul. 30, 1993).
CDC, "Update: Outbreak of acute illness—Southwestern United States, 1993," *Morbidity and Mortality Weekly Report* 42:612–614 (Aug. 13, 1993).
Elliott et al., "Nucleotide Sequence and Expression of the Small (S) RNA Segment of Maguari Bunyavirus," *Virology* 171:516–524 (1989).
Kallio–Kokko et al., "Puumala virus Antibody and Immunoglobulin G Avidity Assays Based on a Recombinant Nucleocapsid Antigen," *Journal of Clinical Microbiology* 31:677–680 (Mar., 1993).
Lundkvist et al., "Immunoglobulin G Subclass Responses against the Structural Components of Puumala Virus," *Journal of Clinical Microbiology* 31:368–372 (Feb., 1993).
Yoo et al., "Genomic comparison among members of Hantavirus group," in *The Biology of Negative Strand Virus,* Mahy & Kolakofsky (Eds.), Elsvier Science Publishers BV (1987).
*Fundamental Virology,* 2nd Ed., 545–564 (1991).
*People Weekly,* 30–33 (Jun. 21, 1993).

*Primary Examiner*—Bradley L. Sisson
*Attorney, Agent, or Firm*—Fitch, Even, Tabin & Flannery

[57] ABSTRACT

The present invention relates to the discovery of a novel Hantavirus. In particular, the present invention relates to nucleic acids of the newly discovered virus and to nucleic acid reagents and antibodies for use in methods of detection and prevention of infection by the virus.

17 Claims, No Drawings

SEQUENCE LISTING (1) GENERAL INFORMATION:

(iii) NUMBER OF SEQUENCES: 12

(2) INFORMATION FOR SEQ ID NO:1:

(i) SEQUENCE CHARACTERISTICS:
      (A) LENGTH: 562 base pairs
      (B) TYPE: nucleic acid
      (C) STRANDEDNESS: single
      (D) TOPOLOGY: linear (ii) MOLECULE TYPE: Nucleic Acid (iii) HYPOTHETICAL: NO (iv) ANTI-SENSE: NO (vi) ORIGINAL SOURCE:
      (A) ORGANISM: Hantavirus
      (B) STRAIN: New (viii) POSITION IN GENOME:
      (A) CHROMOSOME/SEGMENT: S Segment
      (C) UNITS: 562 BP (xi) SEQUENCE DESCRIPTION: SEQ ID NO:1:

```
GACTAAAGCT GGAATGAGCA CCCTCAAAGA AGTGCAAGAC AACATCACTC TCCACGAACA      60

ACAACTCGTG ACTGCCAGGC AGAAGCTCAA AGATGCAGAA AGAGCGGTGG AATTGGACCC     120

CGATGATGTT AACAAAAGCA CATTACAGAG CAGACGGGCA GCTGTGTCTG CATTGGAGAC     180

CAAACTCGGA GAACTTAAGC GGGAACTGGC TGATCTTATT GCAGCTCAGA AATTGGCTTC     240

AAAACCTGTT GATCCAACAG GGATTGAACC TGATGACCAT CTAAAGGAAA AGTCATCATT     300

GAGATATGGA AATGTCCTTG ATGTAAATTC CATTGACTTA GAAGAGCCAA GTGGGCAAAC     360

AGCTGATTGG AAATCCATCG GACTCTACAT TCTAAGTTTC GCATTACCGA TTATTCTTAA     420

AGCCTTGTAC ATGTTATCTA CTAGGGGCCG TCAAACAATC AAAGAAAACA AGGGAACAAG     480

AATTCGATTC AAGGATGATT CATCTTATGA AGAAGTCAAT GGGATACGTA AGCCAAGACA     540

TCTGTATGTT TCTATGCCAA CT                                              562
```

(2) INFORMATION FOR SEQ ID NO:2:

(i) SEQUENCE CHARACTERISTICS:
      (A) LENGTH: 911 base pairs
      (B) TYPE: nucleic acid
      (C) STRANDEDNESS: single
      (D) TOPOLOGY: linear (ii) MOLECULE TYPE: Nucleic Acid (iii) HYPOTHETICAL: NO (iv) ANTI-SENSE: NO (vi) ORIGINAL SOURCE:
      (A) ORGANISM: Hantavirus
      (B) STRAIN: New (viii) POSITION IN GENOME:
      (A) CHROMOSOME/SEGMENT: M Segment
      (C) UNITS: 911 BP (xi) SEQUENCE DESCRIPTION: SEQ ID NO:2:

```
TACGACACCA ACATGTGAGT ATCAAGGCAA CACAGTGTCT GGATTCCAAC GCATGATGGC      60
AACTCGAGAT TCTTTCCAGT CATTCAATGT GACAGAACCA CATATCACTA GCAACCGACT     120
TGAGTGGATT GATCCAGATA GCAGTATCAA AGATCACATT AATATGGTTT TAAATCGAGA     180
TGTTTCCTTT CAGGATCTAA GTGATAACCC ATGCAAGGTT GACCTGCATA CACAATCAAT     240
TGACGGGGCC TGGGGTTCAG GAGTAGGTTT TACGTTGGTA TGTACTGTGG GGCTTACAGA     300
GTGTGCAAAT TTTATAACTT CAATTAAAGC ATGTGATTCT GCCATGTGTT ATGGAGCCAC     360
AGTGACAAAT CTGCTTAGAG GGTCTAACAC AGTTAAAGTT GTTGGTAAAG GTGGGCATTC     420
TGGATCTTTG TTTAAATGCT GCCATGATAC TGACTGTACC GAAGAAGGGT TAGCAGCATC     480
TCCACCACAT TTAGACAGGG TTACAGGCTA TAATCAAATA GATTCTGATT AAAGTTTATG     540
ATGACGGTGC ACCGCCTGTA CAATCAAGTG CTGGTTCACC AAGTCAGGTG AATGGCTGTT     600
GGGAATCCTT AATGGCAATT GGGTGGTAGT TGCTGTTCTG ATTGTAATTT TGATATTATC     660
GATACTCCTT TTTAGCTTTT TTTGTCCTGT CAGAAGTAGA AAGAATAAAG CTAATTAGTG     720
AATATATATG TGAGCAAGAG TATGACAACA TTATTTCATT ATATGTATGT TCTTATATCA     780
ATAACATTTG TATATTCCCA TAACCGAAAT ATTTATACTA ATTTTTATTT TTAAACAAGT     840
ATTAACTAAC CCATTAACAG CTAAAAAAAA CAAATCCTTA ACACCTATAT AATCCCATTT     900
GCTTATTACG A                                                         911
```

(2) INFORMATION FOR SEQ ID NO:3:

(i) SEQUENCE CHARACTERISTICS:
        (A) LENGTH: 2059 base pairs
        (B) TYPE: nucleic acid
        (C) STRANDEDNESS: single
        (D) TOPOLOGY: linear (ii) MOLECULE TYPE: Nucleic Acid (iii) HYPOTHETICAL: NO (iv) ANTI-SENSE: NO (vi) ORIGINAL SOURCE:
        (A) ORGANISM: Hantavirus
        (B) STRAIN: New (viii) POSITION IN GENOME:
        (A) CHROMOSOME/SEGMENT: S Segment
        (C) UNITS: 2059 BP (xi) SEQUENCE DESCRIPTION: SEQ ID NO:3:

```
TAGTAGTAGA CTTCGTAAAA AGCTACTACG ACTAAAGCTG GAATGAGCAC CCTCAAAGAA      60
GTGCAAGACA ACATCACTCT CCACGAACAA CAACTCGTGA CTGCCAGGCA GAAGCTCAAA     120
GATGCAGAAA GAGCGGTGGA ATTGGACCCC GATGATGTTA ACAAAAGCAC ATTACAGAGC     180
AGACGGGCAG CTGTGTCTGC ATTGGAGACC AAACTCGGAG AACTTAAGCG GGAACTGGCT     240
GATCTTATTG CAGCTCAGAA ATTGGCTTCA AAACCTGTTG ATCCAACAGG GATTGAACCT     300
GATGACCATC TAAAGGAAAA GTCATCATTG AGATATGGAA ATGTCCTTGA TGTAAATTCC     360
ATTGACTTAG AAGAGCCAAG TGGGCAAACA GCTGATTGGA AATCCATCGG ACTCTACATT     420
CTAAGTTTCG CATTACCGAT TATTCTTAAA GCCTTGTACA TGTTATCTAC TAGGGGCCGT     480
CAAACAATCA AAGAAAACAA GGGAACAAGA ATTCGATTCA AGGATGATTC ATCTTATGAA     540
GAAGTCAATG GGATACGTAA GCCAAGACAT CTGTATGTTT CTATGCCAAC TGCCCAGTCT     600
```

```
ACAATGAAAG CAGATGAGAT TACTCCCGGG AGGTTCCGTA CAATTGCTTG TGGATTATTC      660

CCAGCCCAAG TCAAAGCAAG GAATATTATC AGTCCTGTCA TGGGTGTGAT TGGCTTTAGT      720

TTTTTTGTGA AAGATTGGAT GGAAAGGATT GATGACTTCC TGGCTGCACG TTGCCCATTT      780

CTGCCTGAGC AGAAAGACCC TAGAGATGCT GCATTGGCAA CTAATAGAGC CTATTTTATA      840

ACACGTCAAT TACAGGTTGA TGAGTCAAAG GTTAGTGATA TTGAGGACCT GATTGCTGAT      900

GCAAGGGCTG AGTCTGCCAC TATATTCGCA GATATTGCTA CTCCTCATTC AGTTTGGGTC      960

TTTGCATGTG CTCCAGATCG TTGTCCACCT ACAGCATTAT ATGTGGCCGG GATGCCGGAA     1020

CTGGGTGCAT TTTTTGCTAT TCTCCAGGAT ATGAGGAACA CCATAATGGC ATCCAAATCT     1080

GTGGGGACAT CTGAAGAGAA ATTGAAGAAG AAATCAGCAT TCTACCAGTC ATACTTAAGA     1140

CGTACTCAGT CAATGGGAAT TCAACTGGAC CAGAAGATAA TCATCTTATA CATGAGCCAT     1200

TGGGAAGAG AGGCCGTGAA TCACTTCCAT CTTGGAGATG ATATGGATCC TGAGCTTAGG     1260

GAACTTGCCC AGACCCTTGT AGATATCAAG GTCAGGGAAA TCTCTAACCA AGAACCACTT     1320

AAACTTTAAG TGGGCAGTAA TCAACTTATA TTCAGGGCAT TATTATAACC AGGGTAATGG     1380

GCACTAATCA GGGTTTATTG CACTAGGGTG GGTTCAAGGG CCAATTATAT CACAGGGTAT     1440

ATAATCTATA TTGTTTAGTG TTATTGTAGT ATTGTATTAT GTATTGTTAG TTAAGCTTAT     1500

TAAATCTTGT TAAGTTTGTT AAGTTTTGTT AAGTTGTATT AAGTTTTGTT AAGTTTCGGT     1560

AAGTCTGTTA AATGTAGTTA ATCTTGATAG TATTAAGTCA TATGTATGGG GGGTGTTTAG     1620

TGTTAAGTCA TTGTTTATTG TTTATTGTTA TCTGTTTAAT GCTAAGTCTA TATGATTTAT     1680

TAATCAAAAT AAGATTTATA TACATAGATT TATTTTATAT ACATAGATTT ATTTTATCAA     1740

CTCATTATCA TCTCTCATCA TTAATCAGGG TTTATAAAAT TTTCTCAGGT CTATCCCTAT     1800

ATTGGAAGAT TGTTCTATTA ACCGTTCAAA CTGGAACTAA CACTGTGACT CTGTAAAGTC     1860

CAGATTATAT TCACATCTGT ATATATGGAT GTAAATTTCG TTCCGTTAAT AGTACATGAC     1920

ACTAATGCTT GCTTTGCTAC TAATTGATTT CTTCATTACA ACAATCTACC TCATTGTCCC     1980

TATCCCCTTC CCTATTACCT CAACAAAACT ACCTCATTAT AAGTAAATTC TTGATTGCTT     2040

TTCAAGGAGT ATACTACTA                                                  2059
```

(2) INFORMATION FOR SEQ ID NO:4:

(i) SEQUENCE CHARACTERISTICS:
        (A) LENGTH: 3696 base pairs
        (B) TYPE: nucleic acid
        (C) STRANDEDNESS: single
        (D) TOPOLOGY: linear (ii) MOLECULE TYPE: Nucleic Acid (iii) HYPOTHETICAL: NO (iv) ANTI-SENSE: NO (vi) ORIGINAL SOURCE:
        (A) ORGANISM: Hantavirus
        (B) STRAIN: New (viii) POSITION IN GENOME:
        (A) CHROMOSOME/SEGMENT: M Segment
        (C) UNITS: 3696 BP (xi) SEQUENCE DESCRIPTION: SEQ ID NO:4:

```
TAGTAGTAGA CTCCGCAAGA AGAAGCAAAC ACTGAATAAA GGAGATACAG AATGGTAGGG       60

TGGGTTTGCA TCTTCCTCGT GGTCCTTACT ACTGCAACTG CTGGGCTAAC ACGGAATCTT      120

TATGAGTTGA AGATAGAATG TCCACATACT GTGGGTTTAG GTCAGGGTTA CGTGACAGGT      180
```

```
TCAGTGGAAA TTACACCTAT TCTCTTAACG CAGGTAGCTG ATCTGAAGAT TGAGAGTTCT      240

TGTAATTTCG ATTTGCATGT CCCGGCTACC ACTACCCAAA AATACAATCA GGTTGACTGG      300

ACCAAAAAAA GTTCAACTAC AGAAAGCACA AATGCAGGTG CAACTACATT TGAGGCTAAA      360

ACAAAAGAGA TAAATTTGAA AGGCACATGT AATATTCCTC CAACTACATT TGAAGCTGCA      420

TATAAATCAA GGAAGACAGT AATTTGTTAT GATTTAGCCT GTAATCAAAC ACATTGTCTT      480

CCTACGGTCC ATTTGATTGC TCCTGTTCAA ACGTGCATGT CTGTGCGGAG CTGTATGATA      540

GGTTTGCTGT CAAGCAGGAT TCAAGTGATA TATGAGAAGA CATACTGCGT TACAGGTCAA      600

TTAATAGAGG GGCTATGTTT CATCCCAACA CATACAATTG CACTCACACA ACCTGGTCAT      660

ACCTATGATA CTATGACATT GCCAGTGACT TGTTTTTTAG TAGCTAAAAA GTTGGGAACA      720

CAGCTTAAGC TGGCTGTTGA GTTAGAGAAA CTGATTACTG GTGTAAGTTG CACAGAAAAC      780

AGCTTTCAAG GTTACTACAT CTGTTTTATC GGGAAACATT CAGAGCCCTT ATTTGTGCCA      840

ACAATGGAGG ATTATAGGTC AGCTGAGTTA TTTACCCGTA TGGTTTTAAA TCCGAGAGGT      900

GAAGATCATG ACCCTGATCA AAATGGACAA GGTTTAATGA GAATAGCTGG GCCTGTTACA      960

GCTAAGGTGC CATCTACAGA AACAACTGAA ACAATGCAAG GAATTGCATT TGCTGGAGCA     1020

CCAATGTATA GCTCTTTCTC AACCCTCGTG AGGAAGGCTG ATCCTGAGTA TGTCTTCTCA     1080

CCAGGTATAA TTGCAGAATC AAATCATAGT GTTTGTGATA AAAAAACAGT ACCCCTTACA     1140

TGGACAGGGT TTTTGGCAGT TTCTGGAGAG ATAGAGAAAA TAACAGGCTG TACAGTCTTC     1200

TGTACATTGG CTGGACCTGG TGCTAGTTGT GAAGCATACT CAGAAACAGG AATCTTTAAT     1260

ATAAGTTCTC CTACTTGTCT AGTGAATAAA GTTCAAAAAT TCAGAGGCTC AGAACAGAGG     1320

ATTAACTTCA TGTGCCAAAG AGTTGATCAA GATGTAGTTG TCTATTGTAA TGGACAAAAG     1380

AAAGTCATTC TTACCAAAAC TCTGGTCATA GGCCAATGCA TTTATACATT CACTAGTTTA     1440

TTCTCACTAA TCCCAGGAGT TGCCCATTCT CTTGCTGTAG AGCTATGTGT TCCAGGCCTT     1500

CATGGCTGGG CTACAACGGC ATTACTGATT ACTTTTTGCT TTGGCTGGCT CCTTATACCG     1560

GCAGTCACCT TAATTATACT GAAGATCCTG AGGTTGCTCA CTTTCTCATG CTCACATTAT     1620

TCCACAGAAT CAAAATTCAA AGTTATCTTA GAAAGGGTTA AGGTTGAATA TCAGAAAACA     1680

ATGGGCTCTA TGGTGTGTGA TATTTGCCAC CACGAATGCG AAACAGCAAA AGAACTTGAA     1740

ACACATAAGA AAAGCTGTCC AGAAGGTCAA TGCCCGTATT GTATGACAAT AACTGAATCC     1800

ACTGAGAGTG CTCTCCAAGC CCATTTTGCA ATCTGTAAGC TAACAAACAG GTTTCAGGAA     1860

AACTTAAAAA AGTCATTGAA ACGCCCAGAA GTACGGAAAG GTTGTTACAG GACACTGGGA     1920

GTTTTTAGAT ACAAGAGCAG ATGTTATGTT GGTTTAGTAT GGGGAATTCT TTTAACAACT     1980

GAACTGATCA TATGGGCAGC CAGTGCAGAC ACCCCTTTAA TGGAGTCTGG TTGGTCTGAC     2040

ACAGCACATG GTGTGGGCAT AATTCCTATG AAGACAGATT GGAGCTTGA TTTTGCATTG     2100

GCCTCATCAT CTTCTTACAG TTATAGGCGA AAGCTTGTTA ATCCTGCTAA TCAAGAAGAA     2160

ACACTCCCTT TTCATTTCCA GTTAGATAAA CAAGTAGTGC ATGCAGAGAT CCAGAACCTA     2220

GGACATTGGA TGGATGGCAC ATTCAACATA AAAACTGCTT TTCACTGTTA TGGGGAGTGT     2280

AAAAAATATG CCTATCCTTG GCAAACAGCC AAGTGTTTCT TTGAAAAGGA TTATCAATAT     2340

GAAACAAGTT GGGGCTGTAA TCCACCAGAC TGTCCAGGGG TAGGTACAGG TTGTACAGCT     2400

TGTGGGGTGT ACCTTGATAA GCTCCGTTCG GTTGGGAAAG CGTACAAGAT AGTATCACTC     2460

AAATATACAC GGAAGGTGTG TATTCAATTA GGAACAGAAC AAACTTGTAA ACATATAGAT     2520

GTAAATGATT GCCTGGTTAC CCCTTCTGTC AAAGTTTGTA TGATTGGTAC TATATCAAAG     2580
```

```
CTCCAGCCAG GTGATACCTT GTTGTTCTTA GGTCCTTTAG AGCAGGGTGG GATCATTCTT      2640

AAGCAATGGT GTACAACATC ATGTGTGTTT GGAGATCCCG GTGATATTAT GTCAACAACA      2700

AGTGGGATGC GGTGCCCAGA ACATACTGGA TCTTTTAGAA AGATCTGTGG GTTTGCTACG      2760

ACACCAACAT GTGAGTATCA AGGCAACACA GTGTCTGGAT TCCAACGCAT GATGGCAACT      2820

CGAGATTCTT TCCAGTCATT CAATGTGACA GAACCACATA TCACTAGCAA CCGACTTGAG      2880

TGGATTGATC CAGATAGCAG TATCAAAGAT CACATTAATA TGGTTTTAAA TCGAGATGTT      2940

TCCTTTCAGG ATCTAAGTGA TAACCCATGC AAGGTTGACC TGCATACACA ATCAATTGAC      3000

GGGGCCTGGG GTTCAGGAGT AGGTTTTACG TTGGTATGTA CTGTGGGGCT TACAGAGTGT      3060

GCAAATTTTA TAACTTCAAT TAAAGCATGT GATTCTGCCA TGTGTTATGG AGCCACAGTG      3120

ACAAATCTGC TTAGAGGGTC TAACACAGTT AAAGTTGTTG GTAAAGGTGG GCATTCTGGA      3180

TCTTTGTTTA AATGCTGCCA TGATACTGAC TGTACCGAAG AAGGGTTAGC AGCATCTCCA      3240

CCACATTTAG ACAGGGTTAC AGGCTATAAT CAAATAGATT CTGATAAAGT TTATGATGAC      3300

GGTGCACCGC CCTGTACAAT CAAGTGCTGG TTCACCAAGT CAGGTGAATG GCTGTTGGGA      3360

ATCCTTAATG GCAATTGGGT GGTAGTTGCT GTTCTGATTG TAATTTTGAT ATTATCGATA      3420

CTCCTTTTTA GCTTTTTTTG TCCTGTCAGA AGTAGAAAGA ATAAAGCTAA TTAGTGAATA      3480

TATATGTGAG CAAGAGTATG ACAACATTAT TTCATTATAT GTATGTTCTT ATATCAATAA      3540

CATTTGTATA TTCCCATAAC CGAAATATTT ATACTAATTT TTATTTTTAT ACAAGTATTA      3600

ACTAACCCAT TAACAGCTAA AAAAAACAAA TCCTTAACAC CTATATAATC CCATTTGCTT      3660

ATTACGAGGC TTTTGTTCCT GCGGAGTCTA CTACTA                               3696

(2) INFORMATION FOR SEQ ID NO:5:

(i) SEQUENCE CHARACTERISTICS:
        (A) LENGTH: 1000 base pairs
        (B) TYPE: nucleic acid
        (C) STRANDEDNESS: single
        (D) TOPOLOGY: linear (ii) MOLECULE TYPE: Nucleic Acid (iii) HYPOTHETICAL: NO (iv) ANTI-SENSE: NO (vi) ORIGINAL SOURCE:
        (A) ORGANISM: Hantavirus
        (B) STRAIN: New (viii) POSITION IN GENOME:
        (A) CHROMOSOME/SEGMENT: L Segment
        (B) UNITS: 1000 BP (xi) SEQUENCE DESCRIPTION: SEQ ID NO:5:

TAATTTACGC TATTTGATCC CAGCTGTCAC ATCATTATAT TCAGGTTATG AGCTCTTAAT        60

AGAAAAATTC TTTGAGCGGC CGTTTAAGAG TGCCTTAGAA GTATATTTAT ATAATATAAT       120

AAAAGCATTG CTTATAAGCC TAGCACAAAA TAATAAGGTA CGATTCTACT CTAAAGTGCG       180

TCTTCTTGGC CTCACTGTCG ATCACTCAAC TGTAGGTGCA AGTGGAGTTT ATCCTTCATT       240

GATGTCTAGA GTTGTTTATA AGCACTATCG TAGTCTTATT TCTGAAGCAA CAACATGTTT       300

CTTTCTTTTT GAAAAGGGCC TACACGGAAA TCTAAATGAG GAGGCTAAAA TACATCTTGA       360

GACTGTAGAG TGGGCAAGAA AATTTGAGGC AAAAGAGAGA AAATATGGAG ACATATTAAT       420

GAGGGAAGGT TACACGATTG ATGCTATACG TGTTGGTGAT GTGCAGGTAG AACAACAATT       480
```

```
ATTTTGTCAA GAGGTTGTGG AGTTAAGTGC AGAAGAACTC AACAAGTATT TACAAGCAAA      540

AAGTCAGGTC TTATCATCCA ATATCATGAA TAAACATTGG GATAAGCCGT ATTTTAGTCA      600

GACAAGGAAT ATAAGTTTAA AGGGTATGTC TGGAGCATTG CAAGAAGATG GACATCTTGC      660

AGCAAGTGTT ACGTTAATTG AGGCAATTAG ATTTTTAAAT AGATCACAGA CTAATCCAAA      720

CGTTATTGAC ATGTATGAAC AGACAAAGCA GCACAAAGCT CAAGCACGTA TTGTGAGGAA      780

ATATCAGCGG ACCGAAGCTG ATAGAGGTTT TTTCATCACT ACTCTCCCGA CAAGAGTCAG      840

GTTAGAAATT ATAGAAGATT ATTATGATGC AATAGCTAGA GTTGTCCCAG AGGAATATAT      900

ATCATACGGA GGAGACAAGA AAATTCTAAA TATACAGACT GCATTAGAGA AGGCATTACG      960

ATGGGCTTCA GGATCATCAG AGGTCATAAC AAGCACAGGA                          1000
```

(2) INFORMATION FOR SEQ ID NO:6:

(i) SEQUENCE CHARACTERISTICS:
        (A) LENGTH: 428 amino acids
        (B) TYPE: amino acid
        (C) STRANDEDNESS: single
        (D) TOPOLOGY: linear (ii) MOLECULE TYPE: Polypeptide (iii) HYPOTHETICAL: NO (iv) ANTI-SENSE: NO (vi) ORIGINAL SOURCE:
        (A) ORGANISM: Hantavirus
        (B) STRAIN: New (viii) POSITION IN GENOME:
        (A) CHROMOSOME/SEGMENT: S Segment
        (B) UNITS: 428 AA (xi) SEQUENCE DESCRIPTION: SEQ ID NO:6:

```
Met Ser Thr Leu Lys Glu Val Gln Asp Asn Ile Thr Leu His Glu Gln
  1               5                  10                  15

Gln Leu Val Thr Ala Arg Gln Lys Leu Lys Asp Ala Glu Arg Ala Val
             20                  25                  30

Glu Leu Asp Pro Asp Asp Val Asn Lys Ser Thr Leu Gln Ser Arg Arg
         35                  40                  45

Ala Ala Val Ser Ala Leu Glu Thr Lys Leu Gly Glu Leu Lys Arg Glu
     50                  55                  60

Leu Ala Asp Leu Ile Ala Ala Gln Lys Leu Ala Ser Lys Pro Val Asp
 65                  70                  75                  80

Pro Thr Gly Ile Glu Pro Asp Asp His Leu Lys Glu Lys Ser Ser Leu
                 85                  90                  95

Arg Tyr Gly Asn Val Leu Asp Val Asn Ser Ile Asp Leu Glu Glu Pro
            100                 105                 110

Ser Gly Gln Thr Ala Asp Trp Lys Ser Ile Gly Leu Tyr Ile Leu Ser
        115                 120                 125

Phe Ala Leu Pro Ile Ile Leu Lys Ala Leu Tyr Met Leu Ser Thr Arg
    130                 135                 140

Gly Arg Gln Thr Ile Lys Glu Asn Lys Gly Thr Arg Ile Arg Phe Lys
145                 150                 155                 160

Asp Asp Ser Ser Tyr Glu Glu Val Asn Gly Ile Arg Lys Pro Arg His
                165                 170                 175

Leu Tyr Val Ser Met Pro Thr Ala Gln Ser Thr Met Lys Ala Asp Glu
            180                 185                 190

Ile Thr Pro Gly Arg Phe Arg Thr Ile Ala Cys Gly Leu Phe Pro Ala
```

-continued

```
                195                 200                 205
Gln Val Lys Ala Arg Asn Ile Ile Ser Pro Val Met Gly Val Ile Gly
    210                 215                 220
Phe Ser Phe Phe Val Lys Asp Trp Met Glu Arg Ile Asp Asp Phe Leu
225                 230                 235                 240
Ala Ala Arg Cys Pro Phe Leu Pro Glu Gln Lys Asp Pro Arg Asp Ala
                245                 250                 255
Ala Leu Ala Thr Asn Arg Ala Tyr Phe Ile Thr Arg Gln Leu Gln Val
                260                 265                 270
Asp Glu Ser Lys Val Ser Asp Ile Glu Asp Leu Ile Ala Asp Ala Arg
                275                 280                 285
Ala Glu Ser Ala Thr Ile Phe Ala Asp Ile Ala Thr Pro His Ser Val
                290                 295                 300
Trp Val Phe Ala Cys Ala Pro Asp Arg Cys Pro Pro Thr Ala Leu Tyr
305                 310                 315                 320
Val Ala Gly Met Pro Glu Leu Gly Ala Phe Phe Ala Ile Leu Gln Asp
                325                 330                 335
Met Arg Asn Thr Ile Met Ala Ser Lys Ser Val Gly Thr Ser Glu Glu
                340                 345                 350
Lys Leu Lys Lys Lys Ser Ala Phe Tyr Gln Ser Tyr Leu Arg Arg Thr
                355                 360                 365
Gln Ser Met Gly Ile Gln Leu Asp Gln Lys Ile Ile Leu Tyr Met
                370                 375                 380
Ser His Trp Gly Arg Glu Ala Val Asn His Phe His Leu Gly Asp Asp
385                 390                 395                 400
Met Asp Pro Glu Leu Arg Glu Leu Ala Gln Thr Leu Val Asp Ile Lys
                405                 410                 415
Val Arg Glu Ile Ser Asn Gln Glu Pro Leu Lys Leu
                420                 425
```

(2) INFORMATION FOR SEQ ID NO:7:

(i) SEQUENCE CHARACTERISTICS:
        (A) LENGTH: 1140 amino acids
        (B) TYPE: amino acid
        (C) STRANDEDNESS: single
        (D) TOPOLOGY: linear (ii) MOLECULE TYPE: Polypeptide (iii) HYPOTHETICAL: NO (iv) ANTI-SENSE: NO (vi) ORIGINAL SOURCE:
        (A) ORGANISM: Hantavirus
        (B) STRAIN: New (viii) POSITION IN GENOME:
        (A) CHROMOSOME/SEGMENT: M Segment
        (B) UNITS: 1140 AA (xi) SEQUENCE DESCRIPTION: SEQ ID NO:7:

```
Met Val Gly Trp Val Cys Ile Phe Leu Val Val Leu Thr Thr Ala Thr
1               5                   10                  15
Ala Gly Leu Thr Arg Asn Leu Tyr Glu Leu Lys Ile Glu Cys Pro His
                20                  25                  30
Thr Val Gly Leu Gly Gln Gly Tyr Val Thr Gly Ser Val Glu Ile Thr
                35                  40                  45
Pro Ile Leu Leu Thr Gln Val Ala Asp Leu Lys Ile Glu Ser Ser Cys
                50                  55                  60
```

```
Asn Phe Asp Leu His Val Pro Ala Thr Thr Gln Lys Tyr Asn Gln
 65                  70                  75                  80

Val Asp Trp Thr Lys Lys Ser Ser Thr Thr Glu Ser Thr Asn Ala Gly
                 85                  90                  95

Ala Thr Thr Phe Glu Ala Lys Thr Lys Glu Ile Asn Leu Lys Gly Thr
            100                 105                 110

Cys Asn Ile Pro Pro Thr Thr Phe Glu Ala Ala Tyr Lys Ser Arg Lys
        115                 120                 125

Thr Val Ile Cys Tyr Asp Leu Ala Cys Asn Gln Thr His Cys Leu Pro
    130                 135                 140

Thr Val His Leu Ile Ala Pro Val Gln Thr Cys Met Ser Val Arg Ser
145                 150                 155                 160

Cys Met Ile Gly Leu Leu Ser Ser Arg Ile Gln Val Ile Tyr Glu Lys
                165                 170                 175

Thr Tyr Cys Val Thr Gly Gln Leu Ile Glu Gly Leu Cys Phe Ile Pro
            180                 185                 190

Thr His Thr Ile Ala Leu Thr Gln Pro Gly His Thr Tyr Asp Thr Met
        195                 200                 205

Thr Leu Pro Val Thr Cys Phe Leu Val Ala Lys Lys Leu Gly Thr Gln
    210                 215                 220

Leu Lys Leu Ala Val Glu Leu Glu Lys Leu Ile Thr Gly Val Ser Cys
225                 230                 235                 240

Thr Glu Asn Ser Phe Gln Gly Tyr Tyr Ile Cys Phe Ile Gly Lys His
                245                 250                 255

Ser Glu Pro Leu Phe Val Pro Thr Met Glu Asp Tyr Arg Ser Ala Glu
            260                 265                 270

Leu Phe Thr Arg Met Val Leu Asn Pro Arg Gly Glu Asp His Asp Pro
        275                 280                 285

Asp Gln Asn Gly Gln Gly Leu Met Arg Ile Ala Gly Pro Val Thr Ala
    290                 295                 300

Lys Val Pro Ser Thr Glu Thr Thr Glu Thr Met Gln Gly Ile Ala Phe
305                 310                 315                 320

Ala Gly Ala Pro Met Tyr Ser Ser Phe Ser Thr Leu Val Arg Lys Ala
                325                 330                 335

Asp Pro Glu Tyr Val Phe Ser Pro Gly Ile Ile Ala Glu Ser Asn His
            340                 345                 350

Ser Val Cys Asp Lys Lys Thr Val Pro Leu Thr Trp Thr Gly Phe Leu
        355                 360                 365

Ala Val Ser Gly Glu Ile Glu Lys Ile Thr Gly Cys Thr Val Phe Cys
    370                 375                 380

Thr Leu Ala Gly Pro Gly Ala Ser Cys Glu Ala Tyr Ser Glu Thr Gly
385                 390                 395                 400

Ile Phe Asn Ile Ser Ser Pro Thr Cys Leu Val Asn Lys Val Gln Lys
                405                 410                 415

Phe Arg Gly Ser Glu Gln Arg Ile Asn Phe Met Cys Gln Arg Val Asp
            420                 425                 430

Gln Asp Val Val Val Tyr Cys Asn Gly Gln Lys Lys Val Ile Leu Thr
        435                 440                 445

Lys Thr Leu Val Ile Gly Gln Cys Ile Tyr Thr Phe Thr Ser Leu Phe
    450                 455                 460

Ser Leu Ile Pro Gly Val Ala His Ser Leu Ala Val Glu Leu Cys Val
465                 470                 475                 480

Pro Gly Leu His Gly Trp Ala Thr Thr Ala Leu Leu Ile Thr Phe Cys
```

-continued

```
                485                 490                 495
Phe Gly Trp Leu Leu Ile Pro Ala Val Thr Leu Ile Ile Leu Lys Ile
                500                 505                 510
Leu Arg Leu Leu Thr Phe Ser Cys Ser His Tyr Ser Thr Glu Ser Lys
            515                 520                 525
Phe Lys Val Ile Leu Glu Arg Val Lys Val Glu Tyr Gln Lys Thr Met
        530                 535                 540
Gly Ser Met Val Cys Asp Ile Cys His His Glu Cys Glu Thr Ala Lys
545                 550                 555                 560
Glu Leu Glu Thr His Lys Lys Ser Cys Pro Glu Gly Gln Cys Pro Tyr
                565                 570                 575
Cys Met Thr Ile Thr Glu Ser Thr Glu Ser Ala Leu Gln Ala His Phe
            580                 585                 590
Ala Ile Cys Lys Leu Thr Asn Arg Phe Gln Glu Asn Leu Lys Lys Ser
        595                 600                 605
Leu Lys Arg Pro Glu Val Arg Lys Gly Cys Tyr Arg Thr Leu Gly Val
    610                 615                 620
Phe Arg Tyr Lys Ser Arg Cys Tyr Val Gly Leu Val Trp Gly Ile Leu
625                 630                 635                 640
Leu Thr Thr Glu Leu Ile Ile Trp Ala Ala Ser Ala Asp Thr Pro Leu
                645                 650                 655
Met Glu Ser Gly Trp Ser Asp Thr Ala His Gly Val Gly Ile Ile Pro
            660                 665                 670
Met Lys Thr Asp Leu Glu Leu Asp Phe Ala Leu Ala Ser Ser Ser Ser
        675                 680                 685
Tyr Ser Tyr Arg Arg Lys Leu Val Asn Pro Ala Asn Gln Glu Glu Thr
    690                 695                 700
Leu Pro Phe His Phe Gln Leu Asp Lys Gln Val Val His Ala Glu Ile
705                 710                 715                 720
Gln Asn Leu Gly His Trp Met Asp Gly Thr Phe Asn Ile Lys Thr Ala
                725                 730                 735
Phe His Cys Tyr Gly Glu Cys Lys Lys Tyr Ala Tyr Pro Trp Gln Thr
            740                 745                 750
Ala Lys Cys Phe Phe Glu Lys Asp Tyr Gln Tyr Glu Thr Ser Trp Gly
        755                 760                 765
Cys Asn Pro Pro Asp Cys Pro Gly Val Gly Thr Gly Cys Thr Ala Cys
    770                 775                 780
Gly Val Tyr Leu Asp Lys Leu Arg Ser Val Gly Lys Ala Tyr Lys Ile
785                 790                 795                 800
Val Ser Leu Lys Tyr Thr Arg Lys Val Cys Ile Gln Leu Gly Thr Glu
                805                 810                 815
Gln Thr Cys Lys His Ile Asp Val Asn Asp Cys Leu Val Thr Pro Ser
            820                 825                 830
Val Lys Val Cys Met Ile Gly Thr Ile Ser Lys Leu Gln Pro Gly Asp
        835                 840                 845
Thr Leu Leu Phe Leu Gly Pro Leu Glu Gln Gly Ile Ile Leu Lys
    850                 855                 860
Gln Trp Cys Thr Thr Ser Cys Val Phe Gly Asp Pro Gly Asp Ile Met
865                 870                 875                 880
Ser Thr Thr Ser Gly Met Arg Cys Pro Glu His Thr Gly Ser Phe Arg
                885                 890                 895
Lys Ile Cys Gly Phe Ala Thr Thr Pro Thr Cys Glu Tyr Gln Gly Asn
            900                 905                 910
```

-continued

```
Thr Val Ser Gly Phe Gln Arg Met Met Ala Thr Arg Asp Ser Phe Gln
        915                 920                 925

Ser Phe Asn Val Thr Glu Pro His Ile Thr Ser Asn Arg Leu Glu Trp
        930                 935                 940

Ile Asp Pro Asp Ser Ser Ile Lys Asp His Ile Asn Met Val Leu Asn
945                 950                 955                 960

Arg Asp Val Ser Phe Gln Asp Leu Ser Asp Asn Pro Cys Lys Val Asp
                965                 970                 975

Leu His Thr Gln Ser Ile Asp Gly Ala Trp Gly Ser Gly Val Gly Phe
                980                 985                 990

Thr Leu Val Cys Thr Val Gly Leu Thr Glu Cys Ala Asn Phe Ile Thr
            995                1000                1005

Ser Ile Lys Ala Cys Asp Ser Ala Met Cys Tyr Gly Ala Thr Val Thr
        1010                1015                1020

Asn Leu Leu Arg Gly Ser Asn Thr Val Lys Val Gly Lys Gly Gly
1025                1030                1035                1040

His Ser Gly Ser Leu Phe Lys Cys Cys His Asp Thr Asp Cys Thr Glu
                1045                1050                1055

Glu Gly Leu Ala Ala Ser Pro Pro His Leu Asp Arg Val Thr Gly Tyr
                1060                1065                1070

Asn Gln Ile Asp Ser Asp Lys Val Tyr Asp Gly Ala Pro Pro Cys
        1075                1080                1085

Thr Ile Lys Cys Trp Phe Thr Lys Ser Gly Glu Trp Leu Leu Gly Ile
        1090                1095                1100

Leu Asn Gly Asn Trp Val Val Val Ala Val Leu Ile Val Ile Leu Ile
1105                1110                1115                1120

Leu Ser Ile Leu Leu Phe Ser Phe Phe Cys Pro Val Arg Ser Arg Lys
                1125                1130                1135

Asn Lys Ala Asn
        1140
```

(2) INFORMATION FOR SEQ ID NO:8:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: Nucleic Acid (iii) HYPOTHETICAL: NO (iv) ANTI-SENSE: NO (xi) SEQUENCE DESCRIPTION: SEQ ID NO:8:

CTCCTTGAAA AGCTACTACG ACTAAAGCTG GAATGA                         36

(2) INFORMATION FOR SEQ ID NO:9:

(i) SEQUENCE CHARACTERISTICS:
        (A) LENGTH: 34 base pairs
        (B) TYPE: nucleic acid
        (C) STRANDEDNESS: single
        (D) TOPOLOGY: linear (ii) MOLECULE TYPE: Nucleic Acid (iii) HYPOTHETICAL: NO (iv) ANTI-SENSE: NO (xi) SEQUENCE DESCRIPTION: SEQ ID NO:9:

```
CAGGTCGACA TTATATCTTT AGTGGTTCTT GGTT                                    34
```

(2) INFORMATION FOR SEQ ID NO:10:

(i) SEQUENCE CHARACTERISTICS:
        (A) LENGTH: 42 base pairs
        (B) TYPE: nucleic acid
        (C) STRANDEDNESS: single
        (D) TOPOLOGY: linear (ii) MOLECULE TYPE: Nucleic Acid (iii) HYPOTHETICAL: NO (iv) ANTI-SENSE: NO (xi) SEQUENCE DESCRIPTION: SEQ ID NO:10:

```
CAGCTGCAGG GAATGAGCAC CCTCAAAGAA GTGCAAGACA AC                           42
```

(2) INFORMATION FOR SEQ ID NO:11:

(i) SEQUENCE CHARACTERISTICS:
        (A) LENGTH: 45 base pairs
        (B) TYPE: nucleic acid
        (C) STRANDEDNESS: single
        (D) TOPOLOGY: linear (ii) MOLECULE TYPE: Nucleic Acid (iii) HYPOTHETICAL: NO (iv) ANTI-SENSE: NO (xi) SEQUENCE DESCRIPTION: SEQ ID NO:11:

```
CAGCTGCAGA TTATATCTTT AGTGGTTCTT GGTTAGAGAT TTCCC                        45
```

(2) INFORMATION FOR SEQ ID NO:12:

(i) SEQUENCE CHARACTERISTICS:
        (A) LENGTH: 26 amino acids
        (B) TYPE: amino acid
        (C) STRANDEDNESS: single
        (D) TOPOLOGY: linear (ii) MOLECULE TYPE: Polypeptide (iii) HYPOTHETICAL: NO (iv) ANTI-SENSE: NO (xi) SEQUENCE DESCRIPTION: SEQ ID NO:12:

```
Met Arg Gly Ser His His His His His His Thr Asp Pro His Ala Ser
1               5                   10                  15

Ser Val Pro Arg Val Asp Leu Glu Gly Met
            20                  25
```

STRAIN OF HANTAVIRUS NUCLEOTIDE SEQUENCES THEREOF RELATED PROBES, PRIMERS AND VECTORS, AND METHODS FOR DETECTION

This application is a file-wrapper-continuation application under 37 CFR 1.62, of prior U.S. application Ser. No. 08/133,591 filed Oct. 7, 1993, now abandoned, which is a continuation-in-part of U.S. Ser. No. 08/084,724 filed Jun. 24, 1993, now abandoned.

BACKGROUND OF THE INVENTION

1. Field of the Invention

The present invention relates to discovery of a novel Hantavirus. In particular, the present invention relates to nucleic acids of the novel Hantavirus and to nucleic acid reagents and antibodies for use in methods of detection and prevention of infection by the new virus.

2. Background Art

Recently, an outbreak of an unknown disease presenting with the abrupt onset of fever, myalgia, headache, cough and finally respiratory failure occurred in the Four Corners Region of the United States. The disease has been clinically termed ARDS (unexplained Adult Respiratory Distress Syndrome). Of the 12 human cases that have been reported, 75% of these patients have died. The outbreak appears to be confined primarily to the Four Corners Region of New Mexico, Arizona and Colorado.

The high mortality associated with ARDS and the unknown etiology of the pathogen created an urgent need to isolate and identify the pathogen and to provide reliable methods for diagnosis, treatment and prevention of the disease. The present invention satisfied that need by identifying a previously unreported strain of Hantavirus as the causative agent of the ARDS outbreak. The present invention also provides methods to diagnose and prevent infection.

SUMMARY OF THE INVENTION

The present invention provides the discovery and isolation of a new virus. This virus is the etiologic agent responsible for the outbreak of the Adult Respiratory Distress Syndrome (ARDS) in the Four Corners Region of the United States. Based upon genetic characteristics, this new virus should be classified in the Hantavirus family.

The present invention also provides isolated nucleic acids and nucleic acid reagents which can be utilized to diagnose and prevent infection of the new virus. Purified polypeptides encoded by the nucleic acids are also provided. These polypeptides can be utilized in methods of diagnosis or as vaccine components for prevention of infection.

Vectors are also provided which comprise the nucleic acids of the present invention. The vectors can be utilized in host expression systems to produce antigenic peptide reagents for diagnostic and prophylactic applications.

The present invention also provides purified antibodies selectively reactive with the new virus of the invention. These antibodies can be used in various diagnostic methods or as a therapeutic.

DESCRIPTION OF THE PREFERRED EMBODIMENTS

The present invention may be understood more readily by reference to the following detailed description of specific embodiments and the examples included therein.

As used in the claims, "a" can mean one or more.

Virus Characterization

In general, Hantaviruses are spherical 28-nm viruses that were initially identified from the feces of rodents. They have distinctive ultrastructural glycoprotein surfaces of 5–10 nm that are embedded in a lipid bi-layered envelope. The negative sensed RNA of the viral genome consists of three fragments generally designated as S, M, and L for the small, medium, and large genome fragments respectively. The S segment encodes a nucleocapsid protein, where as the M segment encodes the surface glycoproteins G1 and G2. (Schmaljohn, C. S. et al., *Fund. Virol.*, 545:545 (1991)). Four types of Hantavirus have been previously identified and are currently designated Hantaan, Seoul, Puumala, and Prospect Hill Virus. Infection with these agents is usually contracted through contact with the feces and urine of infected rodents.

The discovery of the new virus of the present invention (also known as the Four Corners virus (FCV) and the Hantaviral Pulmonary Syndrome Virus (HSV)) arose out of attempts to identify the etiologic agent responsible for the ARDS outbreak. Antibodies to hundreds of potential bacterial and viral pathogens were screened before a weak serologic cross reactivity was detected. Early results of immunological screening (IFA and IgM and IgG ELISA tests) of sera from case-patients suggested the possible involvement of a Hantavirus in this disease outbreak. This was based on limited immune cross-reactivity of sera with known Hantavirus antigens. Using this information, a genetic approach was developed to attempt to identify this virus.

By retrieving the nucleotide sequences of the known Hantaviruses from the GENBANK database and aligning these sequences with one another, we were able to identify regions of shared sequence similarity between these viruses. Oligonucleotide primers targeting these regions of sequence conservation were designed to provide two independent, nested Polymerase Chain Reaction (PCR) assays for the detection of virus RNA, one targeting Hantaan/Seoul-like virus RNA and the other Puumala/Prospect Hill-like virus RNA. Each assay involves two sets of primers. The first reaction utilizes the enzymes reverse transcriptase and Taq polymerase together with plus sense and minus sense virus-specific primers to synthesize a cDNA copy of target viral RNA and then greatly amplify the quantity of these DNA molecules. Utilizing a second pair of primers, the DNA products of the first reaction are further amplified in a second PCR reaction. This greatly increases both the sensitivity and specificity of this detection assay.

Total RNA was extracted from autopsy tissues taken from numerous cases thought to be associated with the Four Corners disease outbreak. Positive PCR bands of the correct size were obtained in the second round reaction with the Puumala/Prospect Hill designed primers with RNA extracted from tissues from three individuals. Direct sequence analysis of these PCR DNA products revealed the presence of a previously unrecognized Hantavirus in these individuals. Genetic sequence comparisons demonstrated that this virus differed from any previously characterized Hantavirus by more than approximately 30%.

Specifically, the nucleic acid sequences of the new virus shown in SEQ ID NO:1 and SEQ ID NO:2 were compared to the genomic segments from the known types of Hantavirus, i.e., Prospect Hill (PHV), Puumula (PUU), Hantaan (HTN), and Seoul (SEO). Prospect Hill virus showed approximately a 70% sequence homology to the new virus. Homology with Puumala was about 69% and about 61% with the Hantaan and Seoul viruses.

A comparison of these findings with the sequence homology that exists between the known Hantavirus types is as follows: Prospect Hill:Puumula is about 70%; Prospect Hill:Hantaan is about 58%; and Prospect Hill:Seoul is about 58%. These data clearly indicate that the virus discovered by the present invention is a new Hantavirus type.

Genetically highly similar viral sequences were PCR amplified from tissue samples taken from Peromyscus spp. rodents trapped in the Four Corners area, suggesting a direct genetic link between the virus in rodents and in clinical cases. Up to 7% nucleotide sequence differences were seen among PCR products from different human cases associated with the Four Corners region outbreak. However, identical viral sequences were consistently obtained for specific individual cases, independent of tissue source or RNA sample preparation, i.e., the sequence variation was not an artifact of the PCR or sequencing methods employed. This level of genetic variation is not uncommon for RNA viruses. We predict that up to approximately 15% nucleotide sequence deviation from the consensus sequence of this newly identified hantavirus can be reasonably expected. Thus, typically genetic variants of the new virus will be greater than 80% homologous, especially greater than about 15% or 10% homologous. To date, the greatest degree of variance between field isolates of the new virus from the current outbreak is about 7%.

The clinical signs and pathology associated with the new virus are also surprisingly different from that of other Hantaviral infections which usually present as an acute hemorrhagic fever with renal syndrome. The ARDS viral agent identified by the present invention instead produced acute respiratory failure and high mortality in young adults.

The present invention provides an isolated virus comprising the nucleotide sequences set forth in the Sequence Listings as SEQ ID NO:1 and SEQ ID NO:2, or genetic variants thereof. By "isolated virus" is meant the virus has been separated from the tissue contaminants with which the virus naturally occurs. By "genetic variants" is meant a virus having sufficient homology to the virus identified by SEQ ID NO:1 and SEQ ID NO:2, such that primers and probes made from the sequences of the genetic variant will selectively hybridize with the virus identified by SEQ ID NO:1 and SEQ ID NO:2. By "selectively hybridize" is meant the nucleic acid does not hybridize with sequences from previously existing hantavirus to prevent an adequate positive hybridization with the virus identified by SEQ ID NO:1 and SEQ ID NO:2. The virus identified by SEQ ID NO:1 and SEQ ID NO:2 is alternatively referred to herein as "the new virus" or as the "Four Corners Virus" (FCV).

Virus Isolation

Briefly, the new Hantavirus of the present invention can be isolated as follows: The materials suspected of containing the virus are ground in sterile tissue culture medium with a mortar and pestle and sterile powdered glass. The suspension is then allowed to adsorb onto cells, e.g., Vero-E6, MA-104, HMEC-1, or other microvascular or large vessel endothelial cell line for 1 or 2 hours and maintenance medium (MEME with 2% heat inactivated FBS) is added and changed every 5 or 7 days. Periodically, the cells are scraped with a rubber policeman or trypsinized from the plastic and dried onto glass slides for fixation and observation by indirect fluorescent antibody microscopy for hantaviral antigens using polyclonal and monoclonal antibodies. The cells are subpassaged every two weeks and allowed to grow to confluence. The material is carried for a minimum of 5 subpassages (6 total passages) before it is considered negative.

Rodents for isolation attempts can be identified by testing blood from individuals and then attempting isolation on the lungs or kidneys (as outlined above) of those rodents found to have antibodies. Rodents are considered good sources for Hantavirus because the rodents are chronically or persistently infected with the virus.

Animal inoculation can also be utilized for viral isolation. In this instance, suckling ICR mice have been inoculated (intracranially and intraperitoneally), Guinea pigs (intraperitoneally) and Mongolian gerbils (intraperitoncally). The tissues are being blind passaged in the rodents and the tissues tested for the presence of Hantavirus antigens and nucleic acids.

Nucleic Acids

The present invention provides the isolated nucleic acids comprising the nucleotide sequences set forth in the Sequence Listing as SEQ ID NO: 1 and SEQ ID NO: 2, and the sequences complementary thereto. The cDNA sequence shown in SEQ ID NO:1 is a 562 bp sequence complementary to RNA derived from the S segment of the genome of the new virus of the present invention. The cDNA sequence shown in SEQ ID NO:2 is a 911 bp sequence complementary to RNA derived from the M segment of the genome of the new virus of the present invention. Thus, the invention includes both DNA having the recited sequences and RNA which corresponds to the DNA.

By "isolated nucleic acid" is meant separated from at least some of other nucleic acids found in the naturally-occurring organism. The nucleic acids of the present invention can include positive and negative strand RNA as well as DNA and is meant to include genomic and subgenomic nucleic acids found in the naturally-occurring organism. The nucleic acids contemplated by the present invention include negative stranded vRNA of the genome, complementary positive stranded cRNA and mRNA, and complementary cDNA produced therefrom and any nucleic acid which can hybridize to or encode the new virus. The nucleic acids of the present invention specifically include RNA from the three genome segments designated small (S), medium (M) and large (L) and nucleic acids complementary thereto.

The present invention also provides the isolated nucleic acids comprising the nucleotide sequences set forth in the Sequence Listings as SEQ ID NO:3, SEQ ID NO:4, and SEQ ID NO: 5, and the sequences complementary thereto. The cDNA sequence shown in SEQ ID NO: 3 is the compete sequence corresponding to the RNA for the S segment of the genome of the new virus. The cDNA sequence shown in SEQ ID NO: 4 is the compete sequence corresponding to the RNA for the M segment of the genome of the new virus. The cDNA sequence shown in SEQ ID NO: 5 is a 1000 bp sequence complementary to RNA for the L segment of the genome of the new virus.

The present invention also provides isolated nucleic acids that are capable of selectively hybridizing with the nucleic acids comprising the nucleotide sequences set forth in the Sequence Listings as SEQ ID NO: 1, SEQ ID NO: 2, SEQ ID NO: 3, SEQ ID NO: 4, and SEQ ID NO: 5, and the sequences complementary thereto. Thus, an isolated nucleic acid capable of selectively hybridizing with or selectively amplifying all regions of the genome of the new virus of the present invention is contemplated. The sequences can be selected based a nucleotide sequence comparison with presently known Hantavirus. Available computer programs can be used to compare the sequence to select the most appropriate sequences for hybridization or amplification.

Modifications to the nucleic acids of the invention are also contemplated as long as the essential structure and function of the polypeptide encoded by the nucleic acids is maintained. Likewise, fragments used as primers or probes can have substitutions so long as enough complementary bases exist for selective hybridization (Kunkel et al., *Methods Enzymol.* 154:367 (1987)).

The nucleic acids described herein can be used to detect the new virus of the present invention in methods such as the polymerase chain reaction, ligase chain reaction, hybridization and the like. Alternatively, these sequences can be utilized to produce an antigenic protein or protein fragment.

In addition, fragments of the nucleic acids described herein can be selected to be homologous with nucleotide sequences present in other human or animal Hantaviruses. Such an nucleotide sequence shared with other Hantaviruses can be used for example to simultaneously detect related strains or as a basis for a multiprotective vaccine.

Nucleic Acid Detection (Diagnosis) Methods

The presence of the new virus described herein can also be determined by detecting the presence of a nucleic acid specific for the new virus as described above and as follows. The present invention provides reagents which can be used in a method of detecting the presence of the new virus in a subject, comprising detecting the presence of the nucleic acid encoding the new virus.

In particluar, the present invention provides a method of detecting the presence of a Hantavirus in a sample. The method comprises amplifying the viral RNA from the sample using an isolated nucleic acid capable of selectively hybridizing with the nucleic acid comprising the nucleotide sequence set forth in the Sequence Listings as SEQ ID NO: 3, or the sequence complementary thereto and detecting the presence of amplification, the presence of amplification indicating the presence of the Hantavirus in the sample.

The present invention also provides a method of detecting the presence of a Hantavirus in a sample, comprising amplifying the viral RNA using an isolated nucleic acid capable of selectively hybridizing with the nucleic acid comprising the nucleotide sequence set forth in the Sequence Listings as SEQ ID NO: 4, or the sequence complementary thereto and detecting the presence of amplification, the presence of amplification indicating the presence of the Hantavirus in the sample.

Also provided is a method of detecting the presence of a Hantavirus in a sample, comprising amplifying the viral RNA using an isolated nucleic acid capable of selectively hybridizing with the nucleic acid comprising the nucleotide sequence set forth in the Sequence Listings as SEQ ID NO: 5, or the sequence complementary thereto and detecting the presence of amplification, the presence of amplification indicating the presence of the Hantavirus in the sample.

Oligonucleotide primers are provided herein. Examples of primers are set forth in the Sequence Listings as SEQ ID NO: 8; SEQ ID NO: 9; SEQ ID NO: 10 and SEQ ID NO: 11. Such primers are suitable for use in the PCR amplification methods provided by the invention and described herein.

The specificity of these sequences for the new virus can be determined by conducting a computerized comparison with known sequences, catalogued in GenBank, a computerized database, using the computer programs Word Search or FASTA of the Genetics Computer Group (Madison, Wis.), which search the catalogued nucleotide sequences for similarities to the nucleic acid in question.

The nucleic acid specific for the new virus can be detected utilizing a nucleic acid amplification technique, such as polymerase chain reaction (PCR) or ligase chain reaction (LCR). Alternatively, the nucleic acid is detected utilizing direct hybridization or by utilizing a restriction fragment length polymorphism. For example, the present invention contemplates a method of detecting the presence of the new virus comprising ascertaining the presence of a nucleotide sequence associated with a restriction endonuclease cleavage site. In addition, PCR primers which hybridize only with nucleic acids specific for the new virus can be utilized. The presence of amplification indicates the presence of the virus. In another embodiment a restriction fragment of a nucleic acid sample can be sequenced directly using, techniques known in the art and described herein and compared to the known unique sequence to detect the new virus. The present invention also contemplates a method of detecting the presence of the new virus by selective amplification by the methods described herein. Alternatively, the new virus can be detected by directly hybridizing the unique sequence with a nucleic acid probe selective for the new virus. Furthermore, the nucleotide sequence could be amplified prior to hybridization by the methods described above.

Alternative probing techniques, such as LCR, involve the use of mismatch probes, i.e., probes which are fully complementary with the target except at the point of the mutation. The target sequence is then allowed to hybridize both with oligonucleotides which are fully complementary and have oligonucleotides containing a mismatch, under conditions which will distinguish between the two. By manipulating the reaction conditions, it is possible to obtain hybridization only where there is full complementarity. If a mismatch is present there is significantly reduced hybridization.

The polymerase chain reaction (PCR) and reverse transcriptase PCR are techniques that amplify specific nucleic acid sequences with remarkable efficiency. Repeated cycles of denaturation, primer annealing and extension carried out with polymerase, e.g., a heat stable enzyme Taq polymerase, leads to exponential increases in the concentration of desired nucleic acid sequences. Given a knowledge of the nucleotide sequence of the new virus as provided herein, synthetic oligonucleotide can be prepared which are complementary to sequences which flank the nucleic acid of interest. Each oligonucleotide is complementary to one of the two strands. The nucleic acid can be denatured at high temperatures (e.g., 95° C.) and then reannealed in the presence of a large molar excess of oligonucleotide. The oligonucleotide, oriented with their 3' ends pointing towards each other, hybridize to opposite strands of the target sequence and prime enzymatic extension along the nucleic acid template in the presence of the four deoxyribonucleotide triphosphlates. The end product is then denatured again for another cycle. After this three-step cycle has been repeated several times, amplification of a nucleic acid segment by more than one million-fold can be achieved. The resulting nucleic acid may then be directly sequenced in order to locate any genetic alteration.

In yet another method, PCR may be followed by restriction endonuclease digestion with subsequent analysis of the resultant products. Nucleotide substitutions can result in the gain or loss of specific restriction endonuclease site. The gain or loss of a restriction endonuclease recognition site facilitates the detection of the organism using restriction fragment length polymorphism (RFLP) analysis or by detection of the presence or absence of a polymorphic restriction endonuclease site in a PCR product that spans the sequence of interest.

For RFLP analysis, RNA is obtained, for example from a tissue sample, blood, gastric specimen, saliva, dental plaque, other bodily fluids of the subject suspected of containing the new virus. DNA amplified from the RNA is digested with a restriction endonuclease, and subsequently separated on the basis of size by agarose gel electrophoresis. The Southern blot technique can then be used to detect, by hybridizaition with labeled probes, the products of endonuclease digestion. The patterns obtained from the Southern blot can then be compared. Using such an approach, the nucleic acid of the new virus is detected by determining the number of bands detected and comparing this number to the number seen with nucleic acid from the new virus.

Similar creation of additional restriction sites by nucleotide substitutions at the disclosed mutation sites can be readily calculated by reference to the genetic code and a list of nucleotide sequences recognized by restriction endonucleases. Single strand conformational analysis (SSCA) offers a relatively quick method of detecting sequence changes which may be appropriate in at least some instances.

In general, primers for PCR and LCR are usually about 20 bp in length and the preferable range is from 15–25 bp. Better amplification is obtained when both primers are the same length and with roughly the same nucleotide composition. Denaturation of strands usually takes place at 94° C. and extension from the primers is usually at 72° C. The annealing temperature varies according to the sequence under investigation. Examples of reaction times are: 20 mins denaturing; 35 cycles of 2 min, 1 min, 1 min for annealing, extension and denaturation; and finally, a 5 min extension step.

Antigen

Purified antigenic polypeptides, or antigenic fragments thereof, encoded by the nucleic acids of the present invention are also contemplated. As used herein, "encoded" is meant to include negative stranded genomic vRNA capable of transcription into positive strand cRNA or mRNA and includes the viral polypeptides specifically encoded by positive sense cRNA or mRNA produced synthetically or found in the naturally-occurring organism. As used herein, "purified" means the antigen is sufficiently free of contaminants or cell components with which the antigen normally occurs to distinguish the antigen from the contaminants or components. Purified antigen from the new virus of the present invention and antigenic fragments thereof are also referred to herein as "the antigen" or "the antigen of the new virus."

In one embodiment, the present invention provides a purified polypeptide comprising the amino acids encoded by the a nucleic acids of the invention. Such nucleic acids include those capable of selectively hybridizing with the nucleotide sequence set forth in the Sequence Listings as SEQ ID NO:1 or SEQ ID NO:2, or a sequence complementary thereto.

In another embodiment, the present invention provides a purified polypeptide encoded by nucleic acids set forth herein, for example nucleic acids capable of selectively hybridizing with the nucleic acids encoded by nucleotide sequences set forth in the Sequence Listings as SEQ ID NO: 3, SEQ ID NO: 4 and SEQ ID NO: 5, or the sequences complementary thereto.

In a preferred embodiment, the invention provides a purified polypeptide comprising the amino acid sequence set forth in the Sequence Listings as SEQ ID NO: 6. Also provided is a purified polypeptide comprising the amino acid sequence sequence set forth in the Sequence Listings as SEQ ID NO: 7.

Naturally, relevant polypeptides are only those encoded by the plus strands. The purified polypeptides can be tested to determine their antigenicity and specificity by the methods taught herein. Antigenic fragments of the antigen can also be synthesized directly or obtained by chemical or mechanical disruption of the virus or larger polypeptides. An immunoreactive fragment is defined as an amino acid sequence of at least about 5 consecutive amino acids derived from the amino acid sequence.

The polypeptide fragments of the present invention can also be recombinant proteins obtained by cloning nucleic acids encoding the polypeptide in an expression system capable of producing the antigenic polypeptide or fragments thereof.

Once the amino acid sequence of the antigen is provided, it is also possible to synthesize, using standard peptide synthesis techniques, peptide fragments chosen to be homologous to immunoreactive regions of the antigen and to modify these fragments by inclusion, deletion or modification of particular amino acids residues in the derived sequences. Thus, synthesis or purification of an extremely large number of peptides derived from the antigen is possible.

The amino acid sequences of the present polypeptides can contain an immunoreactive portion of the antigen attached to sequences designed to provide for some additional property, such as solubility. The amino acid sequences of the polypeptides can also include sequences in which one or more amino acids have been substituted with another amino acid to provide for some additional property, such as to remove/add amino acids capable of disulfide bonding, to increase its bio-longevity, alter enzymatic activity, or alter interactions with gastric acidity. In any case, the peptide must posses a bioactive property, such as immunoreactivity, immunogenicity, etc.

Determining Immnogenicity

The purified polypeptide fragments thus obtained can be tested to determine their immunogenicity and specificity. Briefly, various concentrations of a putative immunogenically specific fragment are prepared and administered to an animal and the immunological response (e.g., the production of antibodies or cell mediated immunity) of an animal to each concentration is determined. The amounts of antigen administered depend on the subject, e.g. a human or a guinea pig, the condition of the subject, the size of the subject, etc. Thereafter an animal so inoculated with the antigen can be exposed to the virus to test the potential vaccine effect of the specific imunogenic fragment. The specificity of a putative immunogenic fragment can be ascertained by testing sera, other fluids or lymphocytes from the inoculated animal for cross reactivity with other closely related Hantaviruses.

Vectors and Hosts

A vector comprising the nucleic acids of the present invention is also provided. The vectors of the invention can be in a host capable of expressing the antigenic polypeptide fragments contemplated by the present invention.

In one embodiment, the present invention provides a vector comprising a nucleic acid complementary to or capable of selectively hybridizing with nucleic acid comprising the nucleotide sequence set forth in the Sequence Listings as SEQ ID NO: 1, or SEQ ID NO: 2.

In another embodiment, the present invention provides a vector comprising nucleic acids set forth herein, for example a nucleic acid complementary to or capable of selectively hybridizing with nucleic acid comprising the nucleotide sequences set forth in the Sequence listings as SEQ ID NO: 3, SEQ ID NO: 4 or SEQ ID NO: 5.

There are numerous *E. coli* (*Escherichia coli*) expression vectors known to one of ordinary skill in the art useful for the expression of the antigen. Other microbial hosts suitable for use include bacilli, such as *Bacillus subtilis*, and other enterobacteriaceae, such as Salmonella, Serratia, and various Pseudomonas species. In these prokaryotic hosts one can also make expression vectors, which will typically contain expression control sequences compatible with the host cell (e.g., an origin of replication). In addition, any number of a variety of well-known promoters will be present, such as the lactose promoter system, a tryptophan (Trp) promoter system, a beta-lactamase promoter system, or a promoter system from phage lambda. The promoters will typically control expression, optionally with an operator sequence, anid have ribosome binding site sequences for example, for initiating and completing transcription and translation. If necessary an amino terminal methionine can be provided by insertion of a Met codon 5' and in-frame with the antigen. Also, the carboxy-terminal extension of the antigen can be removed using standard oligonucleotide mutagenesis procedures.

Additionally, yeast expression can be used. There are several advantages to yeast expression systems. First, evidence exists that proteins produced in a yeast secretion systems exhibit correct disulfide pairing. Second, post-translational glycosylation is efficiently carried out by yeast secretory systems. The *Saccharomyces cerevisiae* pre-pro-alpha-factor leader region (encoded by the MFα-1 gene) is routinely used to direct protein secretion from yeast (Brake et al., "α-factor-directed synthesis and secretion of mature foreign proteins in *Saccharomyces cerevisiae*." Proc. Nat. Acad. Sci. 81:4642–4646 (1984)). The leader region of pre-pro-alpha-factor contains a signal peptide and a pro-segment which includes a recognition sequence for a yeast protease encoded by the KEX2 gene: this enzyme cleaves the precursor protein on the carboxyl side of a Lys-Arg dipeptide cleavage-signal sequence. The antigen coding sequence can be fused in-frame to the pre-pro-alpha-factor leader region. This construct is then put under the control of a strong transcription promoter, such as the alcohol dehydrogenase I promoter or a glycolytic promoter. The antigen coding sequence is followed by a translation termination codon which is followed by transcription termination signals. Alternatively, the antigen coding sequences can be fused to a second protein coding sequence, such as Sj26 or β-galactosidase, used to facilitate purification of the fusion protein by affinity chromatography. The insertion of protease cleavage sites to separate the components of the fusion protein is applicable to constructs used for expression in yeast. Efficient post translational glycosolation and expression of recombinant proteins can also be achieved in Baculovirus systems.

Mammalian cells permit the expression of proteins in an environment that favors important post-translational modifications such as folding and cysteine pairing, addition of complex carbohydrate structures, and secretion of active protein. Vectors useful for the expression of antigen in mammalian cells are characterized by insertion of the antigen coding sequence between a strong viral promoter and a polyadenylation signal. The vectors can contain genes conferring either gentamicin or methotroxate resistance for use as selectable markers. The antigen and immunoreactive fragment coding sequence can be introduced into a Chinese hamster ovary cell line using a methotrexate resistance-encoding vector. Presence of the vector RNA in transformed cells can be confirmed by Southern analysis and production of a cDNA or opposite strand RNA corresponding to the antigen coding sequence can be confirmed by Northern analysis. A number of other suitable host cell lines capable of secreting intact human proteins have been developed in the art, and include the CHO cell lines, HeLa cells, myeloma cell lines, Jurkat cells, etc. Expression vectors for these cells can include expression control sequences, such as an origin of replication, a promoter, an enhancer, and necessary information processing sites, such as ribosome binding sites, RNA splice sites, polyadenylation sites, and transcriptional terminator sequences. Preferred expression control sequences are promoters derived from immunoglobulin genes, SV40, Adenovirus, Bovine Papilloma Virus, etc. The vectors containing the nucleic acid segments of interest can be transferred into the host cell by well-known methods, which vary depending on the type of cellular host. For example, calcium chloride transfection is commonly utilized for prokaryotic cells, whereas calcium phosphate treatment or electroporation may be used for other cellular hosts.

Alternative vectors for the expression of antigen in mammalian cells, those similar to those developed for the expression of human gamma-interferon, tissue plasminogen activator, clotting Factor VIII, hepatitis B virus surface antigen, protease Nexinl, and eosinophil major basic protein, can be employed. Further, the vector can include CMV promoter sequences and a polyadenylation signal available for expression of inserted nucleic acid in mammalian cells (such as COS7).

The nucleic acid sequences can be expressed in hosts after the sequences have been operably linked to, i.e., positioned to ensure the functioning of, an expression control sequence. These expression vectors are typically replicable in the host organisms either as episommes or as an integral part of the host chromosomal DNA. Commonly, expression vectors can contain selection markers, e.g., tetracycline resistance or hygromycin resistance, to permit detection and/or selection of those cells transformed with the desired nucleic acid sequences (see, e.g., U.S. Pat. No. 4,704,362).

Polynucleotides encoding a variant polypeptide may include sequences that facilitate transcription (expression sequences) and translation of the coding sequences such that the encoded polypeptide product is produced. Construction of such polynucleotides is well known in the art. For example, such polynucleotides can include a promoter, a transcription termination site (polyadenylation site in eukaryotic expression hosts), a ribosome binding site, and, optionally, an enhancer for use in eukaryotic expression hosts, and, optionally, sequences necessary for replication of a vector.

Purified Antibodies

A purified antibody selectively reactive with the new virus or immunodominant polypeptides of the present invention, or genetic varients thereof is also provided. The antibodies can be polyclonal or monoclonal. The antibodies can be selectively reactive with a unique epitope of the virus or a viral antigen. The term "reactive" means capable of binding or otherwise associating nonrandomly with an antigen. "Selectively reactive" as used herein describes an antibody or other ligand that does not cross react substantially with any virus or viral antigen other than the one specified, in this case, the new virus of the present invention. Antibodies can be made by may well-known methods (see also, Harlow and Lane, *Antibodies; A Laboratory Manual*, Cold Spring Harbor Laboratory, Cold Spring Harbor, N.Y., pg. 53–281 (1988)). Briefly, purified virus or viral antigen can be injected into an animal in an amount and in intervals sufficient to elicit an immune response. Antibodies can either be purified directly, or spleen cells can be obtained from the animal. The cells are then fused with an immortal cell line and screened for antibody secretion. The antibodies can be used to screen nucleic acid clone libraries for cells secreting the antigen. Those positive clones can then be sequenced as described in the Examples or by other methods (see, for example, Kelly et al., *Bio/Technology*, 10:163–167 (1992); Bebbington et al., *Bio/Technology*, 10:169–175 (1992)).

The antibody can be bound to a substrate or labeled with a detectable moiety or both bound and labeled. The detectable moieties contemplated with the composition of the present invention are those listed below in the description of the diagnostic methods, including fluorescent, enzymatic and radioactive markers.

Antigen Bound to Substrate

A purified virus or antigen of the new virus bound to a substrate and a ligand specifically reactive with the virus or viral antigen are also contemplated. Such a purified ligand specifically reactive with the virus or viral antigen can be an antibody. The antibody can be a monoclonal antibody obtained by standard methods and as described herein.

Serological Detection (Diagnosis) Methods Detecting Antibody with Antigen

The present invention also contemplates a method of detecting the presence of the new virus in a subject, comprising the steps of contacting an antibody-containing sample from the subject with a detectable amount of the virus or an antigenic polypeptide fragment of the virus and detecting the reaction of the fragment and the antibody, the reaction indicating the presence of the new virus.

In particluar, the present invention provides a method of detecting the presence of a Hantavirus, e.g., the FCV virus in a subject. The method comprises contacting an antibody-containing sample from the subject with a detectable amount of a purified polypeptide comprising the amino acid sequence sequence set forth in the Sequence Listings as SEQ ID NO: 6 and detecting the reaction of the polypeptide and the antibody, the reaction indicating the presence of the Hantavirus.

The present invention also provides a method of detecting the presence of a Hantavirus, e.g., the FCV virus in a subject, comprising contacting an antibody-containing sample from the subject with a detectable amount of a purified polypeptide comprising the amino acid sequence sequence set forth in the Sequence Listings as SEQ ID NO: 7; and detecting the reaction of the polypeptide and the antibody, the reaction indicating the presence of the Hantavirus.

In addition, any antigenic polypeptide or unique fragments of the polypeptide set forth herein can be used in such an assay.

Detecting Antigen with Antibody/Ligand

One example of the method of detecting the new virus of the present invention is performed by contacting a fluid or tissue sample from the subject with an amount of a purified antibody specifically reactive with the antigen as defined herein, and detecting the reaction of the ligand with the antigen. It is contemplated that the antigen will be on intact cells containing the antigen, or will be fragments of the antigen. As contemplated herein, the antibody includes any ligand which binds the antigen, for example, an intact antibody, a fragment of an antibody or another reagent that has reactivity with the antigen. The fluid sample of this method can comprise any body fluid which would contain the antigen or a cell containing the antigen, such as blood, plasma, serum, saliva and urine. Other possible examples of body fluids include sputum, mucus, gastric juice and the like.

ELISA

Enzyme immunoassays such as immunofluorescence assays (IFA), enzyme linked immunosorbent assays (ELISA) and immunoblotting can be readily adapted to accomplish the detection of the antigen. An ELISA method effective for the detection of the antigen can, for example, be as follows: (1) bind the antibody to a substrate; (2) contact the bound antibody with a fluid or tissue sample containing the antigen; (3) contact the above with a secondary antibody bound to a detectable moiety (e.g., horseradish peroxidase enzyme or alkaline phosphatase enzyme); (4) contact the above with the substrate for the enzyme; (5) contact the above with a color reagent; (6) observe color change. The above method can be readily modified to detect antibody as well as antigen.

Competitive Inhibition Assay

Another immunologic technique that can be useful in the detection of the new virus or previous infection thereof utilizes monoclonal antibodies (MAbs) for detection of antibodies specifically reactive with antigen to the new virus. Briefly, sera or other body fluids from the subject is reacted with the antigen bound to a substrate (e.g. an ELISA 96-well plate). Excess sera is thoroughly washed away. A labeled (enzyme-linked, fluorescent, radioactive, etc.) monoclonal antibody is then reacted with the previously reacted antigen-serum antibody complex. The amount of inhibition of monoclonal antibody binding is measured relative to a control (no patient serum antibody). The degree of monoclonal antibody inhibition is a very specific test for a particular variety or strain since it is based on monoclonal antibody binding specificity. MAbs can also be used for detection directly in cells by IFA.

Micro-Agglutination Assay

A micro-agglutination test can also be used to detect the presence of antibodies in a subject. Briefly, latex beads (or red blood cells) are coated with the antigen and mixed with a sample from the subject, such that antibodies in the tissue or body fluids that are specifically reactive with the antigen crosslink with the antigen, causing agglutination. The agglutinated antigen-antibody complexes form a precipitate, visible with the naked eye or by spectrophotometer. In a modification of the above test, antibodies specifically reactive with the antigen can be bound to the beads and antigen in the tissue or body fluid thereby detected.

Sandwich Assay/Flow Cytometry/Immunoprecipitation

In addition, as in a typical sandwich assay, the antibody can be bound to a substrate and reacted with the antigen. Thereafter, a secondary labeled antibody is bound to epitopes not recognized by the first antibody and the secondary antibody is detected. Since the present invention provides antigen from the new virus for the detection of infection or convalescent exposure other serological methods such as flow cytometry and immunoprecipitation can also be used as detection methods.

In the diagnostic methods taught herein, the antigen can be bound to a substrate and contacted by a fluid sample such as serum, urine, saliva or gastric juice. This sample can be taken directly from the patient or in a partially purified form. In this manner, antibodies specific for the antigen (the primary antibody) will specifically react with the bound antigen. Thereafter, a secondary antibody bound to, or labeled with, a detectable moiety can be added to enhance the detection of the primary antibody. Generally, the secondary antibody or other ligand which is reactive, either specifically with a different epitope of the antigen or non-specifically with the ligand or reacted antibody, will be selected for its ability to react with multiple sites on the primary antibody. Thus, for example, several molecules of the secondary antibody can react with each primary antibody, making the primary antibody more detectable.

Detectable Moieties

The detectable moiety will allow visual detection of a precipitate or a color change, visual detection by microscopy, or automated detection by spectrometry, radiometric measurement or the like. Examples of detectable moieties include fluorescein and rhodamine (for fluorescence microscopy), horseradish peroxidase (for either light or electron microscopy and biochemical detection), biotin-streptavidin (for light or electron microscopy) and alkaline phosphatase (for biochemical detection by color change). The detection methods and moieties used can be selected, for example, from the list above or other suitable examples by the standard criteria applied to such selections (Harlow and Lane, pg. 319–358 1988).

Vaccines

The virus or viral antigen, e.g., a purified antigenic polypeptide fragment encoded by the nucleic acids of this invention can be used in the construction of a vaccine comprising an immunogenic amount of the antigen and a pharmaceutically acceptable carrier. The vaccine can be the entire antigen, the antigen on the intact new virus, E. coli or other strain, or an epitope specific to the antigen. The vaccine can also be potentially cross-reactive with antibodies to other antigens. The vaccine can then be used in a method of preventing infection with the new virus described herein.

Immunogenic amounts of the antigen can be determined using standard procedures. Briefly, various concentrations of a putative specific immunoreactive epitope are prepared, administered to a subject and the immunological response (e.g., the production of antibodies) of the subject to each concentration is determined.

The pharmaceutically acceptable carrier contemplated herein can comprise saline or other suitable carriers (Arnon, R. (Ed.) Synthetic Vaccines I:83–92, CRC Press, Inc., Boca Raton, Fla., (1987)). An adjuvant can also be a part of the carrier of the vaccine, in which case it can be selected by standard criteria based on the antigen used, the mode of administration and the subject (Arnon, R. (Ed.), Synthetic Vaccines I: 83–92, CRC Press, INC., Boca Raton, Fla., 1987). Methods of administration can be by oral or sublingual means, or by injection, depending on the particular vaccine used and the subject to whom it is administered.

It can be appreciated from the above that the vaccine can be used as a prophylactic or a therapeutic modality. Thus, the invention contemplates methods of preventing or treating infection from the new virus and the associated ARDS diseases by administering the vaccine to a subject.

Accordingly, therefore, the present invention provides a vaccine comprising the FCV, an immunogenic polypeptide or fragments of the polypeptides. Examples of such polypeptides include those derived from a purified polypeptide encoded by the nucleic acid capable of selectively hybridizing with the nucleic acid comprising the nucleotide sequence set forth in the Sequence Listings as SEQ ID NO: 3, SEQ ID NO: 4 or SEQ ID NO: 5, or the sequences complementary thereto. Such a vaccine would naturally include immunogenic amounts of the virus or polypeptide fragments and a pharmaceutically acceptable carrier.

NUCLEOCAPSID PROTEIN EXPRESSION, PURIFICATION, AND USE IN DIAGNOSIS

Materials and Methods

Sera and tissues. Sera from two nephropathia epidemica cases (NE1; NE2), two Korean hemorrhagic fever cases (KHF1; KHF2), five ARDS cases of the Four Corners area (A, B, C, D, and E), five negative control sera (F, G, H, I, and J), and four from rabbits immunized against SEO, HTN, PUU, and PHV were used in the studies. Lung tissue from a fatal ARDS case in the Four Corners (stored at −70° C.) area was used as a Source for viral-specific RNA.

Bacteria and cell lines. The E. coli M15 strain was used for expression. This strain carries the plasmid pREP4 which confers kanamycin resistance upon E. coli cells and encodes the lac repressor (Villarejo, M. R. and Zabin, I.—"β-galactosidase from termination and deletion mutant strains"—J. Bacteriol. 110:171–178 (1974)). Bacteria were grown in LB Medium containing 25 µg/ml kanamycin. The human Hela cell line was used for expression in mammalian cells. Hela cells were cultured in Dulbecco's Modified Eagle Medium (D-MEM) (GIBCO-BRL) containing 5% fetal bovine serum (FBS) (GIBCO-BRL).

Isolation of RNA fromn autopsy material. Total RNA was isolated from infected lung tissue. Material was thawed at 37° C., cut in small pieces, placed on ice, and homogenized in 500 µl of a solution containing 4M guanidine isothiocyanate—25 mM NaCitrate—0.5% sarcosyl to which beta-mercaptoethanol and NaAcetate, pH 4.0, were added to a final concentration of 0.1 M and 0.2 M, respectively, immediately before use. Subsequently, an equal volume (500 µl) of water-saturated phenol and 150 µl of chloroform/isoamyl alcohol (24:1) were added, the mixture was vortexed for 10 sec, incubated on ice for 15 min, and the two phases were separated by spinning at 10,000×g for 20 min at 4° C. The upper phase was removed and incubated with 5 µl of RNAMATRIX (RNaid Kit; Bio 101) for 5 min at room temperature, centrifuged for 30 sec at 10,000×g, and the pellet was washed three times with RNAWASH (RNaid Kit; Bio 101) and resuspended in 50 µl DEPC-treated water. The RNA was eluted by incubation at 55° C. for 5 min and stored in aliquots at −70° C.

Amplification and cloning of the S segment long open reading frame (N-ORF). The N-ORF was synthesized by reverse transcriptase-polymerase chain reaction (RT-PCR) assay followed by a nested PCR. First round amplification was performed using the primers
5'-CTCCTTGAAAAGCTACTACGACTAAAGCTGGAA TGA-3' (set forth in the Sequence Listing as SEQ ID NO: 8) and
5'-CAGGTCGACATTATATCTTTAGTGGTTCTTGGTT-3' (set forth in the Sequence Listing as SEQ ID NO: 9) (containing a SalI recognition site) followed by a second round of amplification using
5'-CAGCTGCAGGGAATGAGCACCCTCAAAGAAGTG CAAGACAAC-3' set forth in the Sequence Listing as SEQ ID NO: 10 and
5'-CAGCTGCAGATTATATCTTTAGTGGTTCTTGGT TAGAGATTTCCC-3' (set forth in the Sequence Listing as SEQ ID NO: 11 (each contain a PstI recognition site). The RT-PCR assay (first round) was performed in a single tube reaction containing 5 µl of total RNA (1/10 of isolated RNA, see above) using a GeneAmp PCR System 9600 thermocycler (Perkin Elmer) by heating to 41° C. for 60 min (reverse transcription), followed by 40 cycles of 94° C. for 40 sec, 37° C. for 40 sec, 72° C. for 3 min (amplification); and 72° C. for 5 min (elongation) [final concentrations in 100 µl reaction volume: 1× Taq-buffer (Promega), 1.7 mM $MgCl_2$ (Promega), 0.2 mM dNTPs (Promega), 350 ng of each primer, 11 U Reverse Transcriptase (Boehringer Mannheim), 5 U Taq-polymerase (Promega)]. For the second round 1 µl of first round material was amplified after a denaturing step of 94° C. for 2 min, by 40 cycles of 94° C. for 40 sec, 41° C. for 40sec, and 72° C. for 3 min followed by 72° C. for 5 min. DNA products were extracted with phenol and chloroform, precipitated with ethanol, cut with PstI, and gel-purified using SPIN-X columns (Costar).

Sodium dodecylsulfate polyacrylamidgel electrophoresis (SDS-PAGE) and immunoblot analysis: Proteins were separated on SDS-PAGE essentially as described by Laemmli, U.

K.—"Cleavage of structural proteins during the assembly of the head of bacteriophage T4"—Nature 227:680–685 (1970). Urea was added to the separating and stacking gels at a final concentration of 2.5 M and 5.0 M, respectively. Proteins were either stained with Coomassie brilliant blue or blotted onto reinforced nitrocellulose membranes (BA-S 85; Schleicher & Schuell) using a semi-dry blot technique (Khyse-Anderson, J.—"Electroblotting of multiple gels: a simple apparatus without buffer tank for rapid transfer of proteins from polyacrylamide to nitrocellulose"—J. Biochem. Biophys. Methods 10:203–210 (1984)). For immunoblot analysis, membranes were blocked overnight at 4° C. with 5% skim milk in phosphate-buffered saline (PBS), pH 7.2, containing 0.1% TWEEN® 20 (polyoxyethlenesorbitan monolaurate). Electroblots were reacted with polyclonal sera listed above as previously described (Sanchez, A., D. Y. Pifat, R. H. Kenyon, C. J. Peters, J. B. McCormick, and M. P. Kiley—"Junin virus monoclonal antibodies: characterization and cross-reactivity with other arenaviruses"—J. Gen. Virol. 70:1125–1132 (1989)).

In vitro translation: For in vitro translation, the N-ORF was ligated into the Pst I site of the plasmid pTM1 under the control of the T7 RNA polymerase promotor (pTM1-Nfc). Approximately 1 $\mu$g of circular plasmid DNA was used for transcription and translation in the TNTTM coupled reticulocyte lysate system by the protocol of the manufacturer (Promega). The [$^{35}$S]methionine-labeled products were immunoprecipitated using polyclonal sera listed above as described earlier (Sanchez, A. and Kiley, P.—"Identification and analysis of Ebola virus messenger RNA"—Virology 157:414–420 (1987)), separated on 10% SDS-PAGE, and detected by fluorography.

Expression in mammalian cells: Hela cells, cultured in 6-well plates until a confluency of approximately 70%, were infected in D-MEM/2% FBS with a recombinant vaccinia virus, expressing T7 RNA polymerase (VVT7), at a multiplicity of infection (m.o.i.) of 1 to 5 plaque forming units (p.f.u.)/cell. For transfection, 1 $\mu$g circular pTM1-Nfc DNA in 50 $\mu$l water was added dropwise to an equal volume of Lipofectin (GIBCO BRL) (diluted 1:1 in water), incubated for 15 min at room temperature, and added to 1 ml D-MEM/-FBS. The transfection mixture was added to the VVT7-infected Hela cells which were washed twice before in D-MEM/-FBS. 5 hrs posttransfection (37° C.) 2 ml of D-MEM/FBS were added (final concentration of FBS 2%) and incubation was continued at 37° C. for 20 hrs. Cells were washed once with PBS, lyzed in RIPA buffer [20 mM 2-[N-morpholino]ethanesulfonic acid (MES), 55 mM Tris, 200 mM NaCl, 10 mM EDTA, 1% (v/v) SDS (pH 7.8), 1% (v/v) TRITON® X-100 (polyoxyethalene ether) TRASYLOL (aprotinin), 5% (v/v), 1 mM Phenylmethylsulfonyl fluoride (PMSF), 10 mM iodoacetamide], boiled for 10 min, and stored at 20° C. [$^{35}$S]methionine-labeled producte were immunoprecipitated using the polyclonal sera listed above as described earlier (Sanchez and Kiley, 1987).

Indirect immnunofluorescence assay (IFA): Hela cells, cultured on Lab-Tek Chamber Slides (Nunc. Inc.) or 6-well plates were infected with VVT7 followed by transfection with pTM1-Nfc or pTM1 (negative control) as desribed above. 14 hrs post-transfection, cells were washed with PBS, proceeded for IFA, and reacted with the polyclonal sera listed above as described elsewhere (Johnson, D. M., L. H. Elliott, and D. L. Heymann—"Preparation of polyvalent viral immunofluorescent intracellular antigens and use in human serosurveys"—J. Clin. Microbiol. 14:527–529 (1981)).

Expression in *E. coli* and purification of reombinant protein: The N-ORF was ligated into the Pst I site of the plasmid vector pQE-31 (Bujard, H., R. Gentz, M. Lanzer, D. Stüber, M. Müller, I. Ibrahimi, M. T. Häuptie, and B. Dobberstein—"A T5 promotor based trainscription-translation system for the analysis of proteins in vivo and in vitro"—Methods in Enzymology 155:416–433 (1987); St über, D., W. Bannwarth, J. R. L. Pink, R. H. Meloen, and H. Matile—New B cell epitopes in the plasmodium falciparum malaria circumsporozoite protein"—Eur. J. Immunol. 20:819–824 (1990); Stüber, D., H. Matile, and G. Garotta—"System for high-level production in *Escherichia coli* and rapid purification of recombinant proteins: application to epitope mapping, preparation of antibodies, and structure-function analysis—In: Letkovits, I. and Permis, B. (eds.) Immunological Methods, Vol. IV:121–152 (1990)) (pQE-Nfc) and transformed into the the *E. coli* strain M15. Transformants, which grew in the presence of 100 $\mu$g/ml ampicillin and 25 $\mu$g/ml kanamycin, were screened for expression of recombinant proteins as described in the protocol provided by the manufacturer (Diagen; "The QIAexpressionist"). Large scale preparations were done in 500 ml volumes, expression was induced at an $OD_{600}$ of 0.7 by isopropyl-D-thiogalactopyranoside (IPTG) (2 mM), and cultures were harvested 4 hrs post-induction by centrifugation at 4,000×g at 4° C. for 10 min. The recombinaint protein, expressed as a fusion protein with an amino-terminal histidine tag was purified by Ni-NTA resin affinity chromatography (Diagen) using denatured and native conditions as described in a protocol provided by the manufacturer (Diagen; "The QIAexpressionist"). For purification using denatured conditions, cells were resuspended and lyzed in a buffer containing 6M guanidine hydrochloride—0.1M $NaH_2PO_4$—0.01 M Tris—pH adjusted to 8.0 with NaOH (5 ml per gram net weight). Elution of recombinant proteins was performed by a pH gradient of 6.5, 5.9, and 4.5. For purification using native conditions, cells were resuspended in a bufter containing 50 mM $NaH_2PO_4$—300 mM NaCl—pH adjusted to 8.0 with NaOH (5 ml per gram net weight), frozen overnight at 20° C., thawed in cold water, incubated with 1 mg/ml lysozyme for 30 min on ice, sonicated at 4° C., and drawn through a narrow gauge syringe needle for several times. Elution of recombinant proteins was performed with a 30 ml gradient of 0–0.5 M imidazole. Aliquots of the collected fractions (4 ml) were separated on 10% SDS-PAGE and analyzed by Cooimassie brilliant blue staining or immunoblot as described above. Samples of fractions containing imidazole were heated at 37° C. for 10 min instead of boiling (imidazole partially hydrolizes acid labile bonds) prior to loading on gels.

Enzyme-linlked immunosorbent assay (ELISA):—IgG ELISA. Polivinyl chloride microtiter plates were coated overnight at 4° C. with different antigens diluted in PBS (pH 7.2). The antigen dilutions were determined by checkerboard titration with reference sera. The recombinant *E. coli* expressed N protein of FCV and the negative *E. coli* expressed control antigen (pQE-Nfc of FCV, opposite orientation), both purified under denatured conditions, were used at a 1:5000 dilution (30 ng/well). Heterologous viral antigens (PHV, PUU, SEO, HTN) were made as previously described by detergent/basic buffered extraction of infected and uninfected Vero-E6 cells (Ksiazek, T. G., P. E. Rollin, P. B. Jahrling, and C. J. Peters—"Enzyme-linlked immunosorbent assays for the detection of antibodies to Ebola viruses"—Am. J. Trop. Med. Hyg., submitted (1993)). Unbound antigen was removed by washing three times with PBS, 0.1% TWEEN® 20 (polyoxylenesorbitan monolaurate (v/v) (PBS-Tw). Sera were diluted 1:100 and 4-fold through 1:102400 in 5% skim milk in PBS-Tw and reacted with the antigen. Bound IgG was detected with a mouse anti-human IgG (γ-chain specific, Accurate Chemical) conjugated to horseradish peroxidase and $H_2O_2$-ABTS substrate. Optical densities at 410 nm ($OD_{410}$) were recorded on a microplate spectrophotometer and the $OD_{410}$ of the corresponding negative control antigen was substratced to yield the adjusted OD410 value.—IgM ELISA. IgM from serum samples was captured with goat anti-μ (TAGO) adsorbed to microtiter plates and the captired IgM was reacted with viral antigens. Heterologous antigens (PHV, PUU, SEO, HTN) were made from infected and uninfected Vero-E6 cells by several cycles of freeze-thawing followed by sonication. The homologous recombinant *E. coli* expressed N protein of FCV and the *E. coli* expressed negative control antigen (see above) were used in a 1:50 (3 μg/well) dilution. The captured viral antigen was detected with either polyclonal hyperimmune rabbit sera or a monoclonal antibody followed by anti-rabbit or anti-mouse antibodies conjugated with horseradish peroxidase and $H_2O_2$-ABTS substrate. Optimal dilutions of all reagents were determined by checkerboard titration with early convalescent sera. Optical densities were recorded as described above to yield the adjusted $OD_{410}$.

Results

Generation of the N-ORF and in vitro expression: The long ORF of the FCV S segment is 1284 nucleotides in length and extends from the first AUG start codon at position 43–45 to the the stop codon UAA at position 1327–1329. This AUG start codon is in a favorable contex to serve as an initiation codon for eukaryotic ribosomes (Kozak, M.—"Point mutations define a sequence flanking the AUG initiator codon that modulates translation by eukaryotic ribosomes" Cell 44:283–292 (1986)). The ORF encodes the N protein, which is 428 amino acids long and has a calculated MW of 47 kDa. The N-ORF was synthesized by a nested RT-PCR assay using a tirst set of unspecific primers, deduced from a comparison of PUU (Vapalahlti, O., H. Kallio-Kokko, E. M. Salonen, M. Brummer-Korvenkontio, and A. Vaheri—"Cloning and sequencing of Puumala viris Sotkamo strain S and M segments: evidence for strain variation in hantaviruses and expression of the nucleocapsid protein"—J. Gen. Virol. 73:829–838 (1991)) and PHV (Parrington, M. A. and Kang, C. Y.—"Nucleotide sequence analysis of the S genome segment of Prospect Hill virus: comparison with the prototype Hantavirus"—Virology 175:167–175 (1990)) S segment sequences, which were predicted to amplify a DNA fragment of 1329 bp in length. For the second round a set of primers (specific 3' end primer, semispecific 5' end primer) were used which amplified a fragment of 1299 bp. The nested RT-PCR assay was necessary since a single round RT-PCR assay with any of the primer sets and their possible combinations failed to amplify a visuable DNA band. The N-ORF wais ligated into the vector pTM1 downstream of the T7 RNA-polymerase promotor, transcribed by T7 RNA polymerase, and translated in the presence of [$^{35}$S] methionine by a rabbit reticulocyte-lysate. Translation resulted in the synthesis of two products, the most prominant of which showed a size close to that predicted for the FCV N protein, as deduced from SDS-PAGE analysis. The smaller product migrated as a 27 kDa protein and could be generated by internal initiation within the ORF. Four in-frame AUG codons are located downstream of the start codon [position 460–462; 483–485; 700–702; 739–741; ] which could generate a protein of about 27 kDa in size, however, only the one at position 700–702 is in a good contex for translation initiation (Kozak, 1986). The translation products were immunoprecipitated by several ARDS case sera from the Four Corners area, which indicates that the protein produced contains epitopes of the authentic viral N protein.

Transient expression of the N-ORF. A system based on the expression of bacteriophage T7 RNA polymerase in the cytoplasm of mammalian cells by a recombinant vaccinia virus (VVT7) was used to drive the expression of FCV N-ORF cloned in a pTM1 plasmid (pTM1-Nfc) downstream of the T7 RNA polymerase promotor (Fuerst, T. R., E. G. Niles, F. W. Studier, and B. Moss—"Eukaryotic transiet-expression system based on recombinant vaccinia virus that synthesizes bacteriophaze T7 RNA polymerase"—Proc. Natl. Acad. Sci USA 83:8122–8126 (1986); and Fuerst, T. R., P. L. Earl, and B. Moss—"Use of a hybrid vaccinia virus-T7 RNA polymerase system for expression of target genes"—Mol. Cell. Biol. 7:2538–2544 (1987)). Hela cells (70% confluent) were infected with VVT7 at a m.o.i. of 1 to 5 p.f.u./cell and transfected with 1 μg pTM1-Nfc. Expression was analyzed by immunoblot with an ARDS case serum of the Four Corners area (serum A; see above) and metabolic labeling with [$^{35}$S]methionine. A single protein was specifically recognized by serum A in immunoblot analysis and RIP which was not present in the negative control (pTM1-Nfc opposite orientation) and non-transfected, VVT7-infected cells. The protein showed a $M_r$ of approximately 50 kDa and comigrated with the larger in vitro translation product, but migrated faster than the *E. coli* expressed N protein as discussed below. Degradation products were not detected in immunoblot analysis or RIP assays. IFA of cells expressing the N protein (VVT7 system) showed that it was found exclusively perinuclear in the cytoplasm and was observed as an inclusion-type of staining pattern.

Expression of the N-ORF in *E. coli*: The N-ORF was ligated into the Pst I site of the plasmid pQE-31 downstream of the Ribosom binding site, the AUG start codon, and a 6× histidine tag, and transformed into *E. coli*, strain M15 carrying the plasmid pREP4. The correct orientation was confirmed by restriction endonuclease digest (BamHI) and sequencing. In addition, the entire ORF was sequenced in order to exclude point mutations, insertions, or deletions. Due to the construction of the pQE-31 vector, the *E. coli* expressed N protein is a fusion protein which consists of the entire N protein sequence and a 25 amino acid long polypeptide at the amino terminus, which shows the following sequence: $NH_2$-Met-Arg-Gly-Ser-<u>His-His-His-His-His-His</u>-Thr-Asp-Pro-His-Ala-Ser-Ser-Val-Pr o-Arg-Val-Asp-Leu-Gln-Gly-Met---(N-protein)---COOH (histidine tag underlined) (as set forth in the Sequence Listing as SEQ ID NO: 12). Expression from the pQE vector is rapidly induced by the addition of IPTG, which inactivates the repressor encoded by the plasmid pREP4. Histidine tags show an affinity for Ni-NTA resin that is stronger than the affinity between antibodies and antigens or enzymes and substrates and thus remain bound to the resin under relatively stringent wash conditions. The tag was used to purify the N protein by metal chelate affinity chromatography. Transformants were screened for expression and presence of the histidine tag by a rapid small-scale purification protocol. Expression was varified by Coomassie-staining and immunoblot analysis using serum A (see above). As already mentioned above, the *E. coli* expressed N protein is larger (~3 kDa) than the N expressed in the other system due to the additional 25 amino acids contributed by the fusion component. The expression levels varied greatly between different colonies of transformed cells. Those expressing high levels of N (approximately 30 to 40% of total cellular proteins) were used to evaluate expression in varying growth media (2YT, LB) and to determine the peak time of expression post-induction. A single clone was selected for large scale production of N protein and showed maximum levels of expression in LB medium at 4 hr postinduction. These conditions were used to propagate this clone in a 500 ml culture that was induced when an $OD_{600}$ of 0.7 to 0.8 was reached and expression was proceeded for 4 hr. Purification of native and denatured forms of the N protein was done by Ni-NTA resin affinity chromatography. Protein elution fractions were analyzed on 10% SDS-PAGE by either Coomassie staining or immunoblot analysis using serum A. Denatured N protein was eluted primarily at pH 4.5. However, a lesser amount of protein was eluted from the column at pH 5.9. Binding to the resin was very efficient, and only trace amounts of N protein could be still detected in the original loading buffer and wash solutions (pH 8.0 and pH 6.3). N protein was complete eluted at pH 4.5 and no loss was due to tightly bound protein to the resin. The major fraction eluted at pH 4.5 was calculated to contain 4.5 mg protein which was more than 85% pure. Small amounts of breakdown products of expressed N protein were detected in the major fractions (<5% of total) by immunoblot analysis.

Purification under native conditions showed that the expressed N protein was localized in the cytoplasm. The bound protein was eluted with increasing concentrations of imidazole (up to 0.5 M), which competes with the bound histidine-tagged protein, and most of the protein was eluted with 0.2 M imidazole. Native bound N protein was completely eluted with 0.4 M imidazole. The amount of native purified protein by this method was much less (0.5 mg) but more than 85% pure. Only small amounts of degradation products were detected by immunoblot analysis and no further degradation was detected after purification and during storage of the purified protein.

Antigenic properties of recombinant N protein. The *E. coli* expressed N protein, purified tinder denatured conditions as described above, and N protein expressed in the VVT7 system were characterized in immunoblot, RIP, ELISA, and IFA to evaluate their potential for use in diagnostic assays. For this purpose a series of positive, negative, and control sera listed above (Materials and Methods) were used. The results are summarized in Table 1. All positive case sera from the Four Corners area (A, B, C, D, E) reacted strongly in immunoblot assays with both sources of expressed N protein. Two NE case sera cross-reacted with both antigens whereas the two KHF case sera did not. All rabbit antisera showed cross-reactivity with both antigens, but anti-HTN showed only weak reactivity. RIPs were performed with VVT7-derived expressed N protein. However, only case sera A and B efficiently immunoprecipitated the antigen under the conditions given (Table 1). The negative sera (F, G, H, I, J) were unreactive in all assays which were examined independent of the source of antigen. IFA of all five Four Corners case sera reacted strongly and three (A, B, E) showed high titers of >320 (Table 1). Again, both NE case sera cross-reacted with the antigen (NE2 had a comparable titer of 320) and both KHF case sera failed to detect the antigen. *E. coli* expressed antigen was evaluated in IgM and IgG-ELISA using purified denatured N protein at a concentration of 3 μg/well and 30 ng/well, respectively, to coat microtiter plates. All Four Corners case sera reacted specifically with the antigen and were positive either for IgM and/or IgG. As was found with the other assays, the NE case sera cross-reacted in the ELISA, whereas the KHF case sera did not. The anti-PUU and anti-PHV sera showed ELISA-titers comparable to those of the Four Corners case sera, and the anti-HTN again showed the lowest cross-reactivity. The native N protein was also tested in IgM and IgG-ELISA, but did not show any difference in antigenicity compared to the denatured antigen.

The *E. coli* expressed N protein, purified under denatured conditions, was further tested in comparison to heterologous antigens (SEO, HTN, PUU, PHV) to evaluate the specificity and sensitivity in ELISA. For preparation of heterologous antigens, Vero-E6 cells were infected with the different serotype viruses and infected cultures showing a cytopathogenic effect of approximately 70% were harvested as described in "Material and Methods; enzyme-linked immunoadsorbent assay". An *E. coli* clone, carrying the N-ORF in the opposite orientation, and uninfected Vero-E6 cells, treated and harvested at the same time, served as negative controls. The antigens were coated to ELISA-plates and a serial dilution of 1:2 (beginning with 1:100) of the same set of sera discussed before (see above) were used for titration in an IgG-ELISA. The homologous, recombinant antigen usually produced higher optical density values compared to the four heterologous antigens. The PHV antigen was nearly as recombinant homologous antigen followed by PUU. HTN and SEO failed to detect antibodies in several of the Four Corners case sera and are not siuted as antigens for diagnosis of this new hantavirus. The use of the recombinant homologous antigen increased the sensitivity of the IgG-ELISA demonstrated by the detection of cases with very low antibody titers which were unreactive with the PHV and PUU antigens.

Discussion

The outbreak of acute respiratory illness in the Four Corners area of the United States was shown by the present invention to be associated with a novel RNA virus which belongs to the genus Hantatvirus of the family Bunyaviridae, however, a homologous antigen for diagnosis is not available.

The N-ORF of FCV was synthesized by a nested RT-PCR assay and expressed in vitro using a rabbit-reticulocyte-lysate, in Hela cells using T7 RNA polymerase derived from a recombinant vaccinia virus, and in *E. coli* as a fusionprotein with an amino-terminal histidine tag. Immunological characterization of the expressed FCV N proteins clearly demonstrated that the expressed ORF codes for a unknown hantaviral N protein. The recombinant N proteins migrated on SDS-PAGE as expected from the deduced amino acid sequence with a $M_r$ of about 50 kDa. The *E. coli* expressed N protein showed a slightly increased $M_r$ due to an amino-terminal fusionpart of 25 amino acids. The protein size is nearly identical with the sizes of all known hantaviral N proteins (Antic, D., C. Y. Kang, K. Spik, C. S. Schmaljohn, O. Vapalahti, and A. Vaheri—"Comparison of the deduced gene products of the L, M and S genome segments of hantaviruses"—Virus Res. 24:35–46 (1992)). The FCV N protein aligns to 94% with the consensus sequence of all hantaviral N proteins (Antic et al., 1992).

Transient expression of the N protein in Hela cells derived by vaccinia-expressed T7 RNA polymerase showed a strictly cytoplasmic localization of the antigen. The inclusion-like immunostaining pattern, primarily perinuclear, can represent inclusions formed by spontaneous aggregation of expressed N protein as could be shown for other expressed nucleocapsid proteins of negative-strand RNA viruses (Sprague, J., J. H. Condra, H. Arnheiter, and R. A. Lazzarini—"Expression of a recombinant DNA genc coding for the vesicular stomatitis virus nucleocapsid protein"—J. Virol. 45:773–778 (1983); Spehner, D., A. Kirn, and R. Drillien—"Assembly of nucleocapsidelike structures in animal cells infected with a vaccinia virus recombinant encoding the measles virus nucleoprotein"—J.

Virol. 65:6296–6300 (1991)). Although vaccinia-expressed proteins are not the first choice for a diagnostic antigen, we examined the use of cell lysates as antigens for immunoblot and IFA. Suprisingly, in both assays only low background activity against vaccinia proteins could be detected with all human sera tested in the assays (Table 1). Preliminary data on IFAs also demonstrated that the sensitivity of the homologous recombinant antigen is higher compared to heterologous antigen used so far for IFA. The use in IFA can be utilized since this is a quick and simple assay which was demonstrated to be a useful tool for diagnosis in the field.

Expression of the N-ORF in *E. coli* revealed high levels of recombinant N protein located in the cytoplasm. The expression as a fusion protein with an amino-terminal histidine tag allowed purification by a single step of Ni-NTA resin affinity chromatography and yielded substantially pure recombinant N protein. The recombinant protein could be purified under native as well as denatured conditions, however, yields of expressed N protein were decreased by lysis under native conditions. The loss could be due to aggregation of N protein in the cytoplasm which are not solubilized under non-denatured conditions. This would be supported by the fact that N protein was eluted over a broader pH range indicating monomeric and oligomeric forms and accordingly with different numbers of histidine tags. In addition, transient expression in Hela cells also seemed to result in formation of N protein aggregates.

Purified N Protein was characterized in several immunological assays demonstrating the specificity of the recombinant antigen (Table 1). However, some cross-reactivities with sera of all serological groups of hantaviruses known to cause HFRS and anti-PHV were observed. Serological cross-reactivity was expected with anti-PUU and anti-PHV sera since N proteins of both show a high degree of homology to the N protein of FCV. The relatively high degree of cross-reactivity with anti-SEO sera was suprising if one considers the lower degree of homology between the N proteins of SEO and FCV. Human anti-HTN sera did not cross-react with the FCV antigen (rabbit anti-HTN sera showed some cross-reactivity) which can be explained by the fact that FCV and HTN are genetical the most diverse serotypes of the genus. Thus, such regions can be used to avoid cross-reactivity. Cross-reactivity, primarily to the N protein, among the different serotype groups is a known phenomenon for hantaviruses (Sheshberadaran, H., B. Miklasson, and E. A. Tkachenko—"Antigenic relationship between hantaviruses analysed by immunoprecipitation"—J. Gen. Virol. 69:2645–2651 (1988); Wang, M., C. Rossi, and C. S. Schmaljohn—"Expression of non-conserved region of the S genome segment of three hantaviruses: evaluation of the expressed polypeptides for diagnosis of haemorrhagic fever with renal syndrom"—J. Gen. Virol 74:1115–1124 (1993)). This may be reflected in the finding of two conserved regions among all known hantaviral N protein sequences located at the carboxy-terminal end (last 124 amino acids) and between amino acids 80 to 210 with 93.8% and 65.5% homology, respectively.

In general, comparative studies by ELISA and IFA using either homologous recombinant N protein expressed in *E. coli* or heterologous antigen revealed in good agreement. However, the use of recombinant homologous N protein improved the specificity and sensitivity of ELISA and IFA in several cases compared to PHV, the most closely related heterologous antigen;. Preliminary data on larger numbers of human and rodent sera to confirm the higher sensitivity of the homologous antigen. The higher sensitivity can lead to an earlier diagnosis and thus provide for an earlier treatment of patients. A difference in the use of N protein purified under denatured or native conditions was not observed. Both sources of antigen worked equivalently in IgM and IgG-ELISA. The fusion polypeptide of 25 amino acids at the amino terminus and especially the histidine tag lack of interference with the ELISA was demonstrated by the low background activity of the assay with all tested negative sera. This is in line with previous observations of proteins expressed and purified with histidine tags which have never been found to interfere with the structure or function of the purified proteins (Stüber et al., 1990; Takacs, B. J. and Girard, M. F.—"Preparation of clinical grade proteins produced by recombinant DNA technologies"—J. Immunol. Methods 143:231–240 (1991)).

Therefore, *E. coli* expression of the N-ORF resulted in high levels of recombinant N protein. The attachment of a histidine tag at the amino terminus of the N protein provided a simple and very efficient way of purification using a single step affinity chromatography and resulted in >85% pure recombinant protein. The expressed protein was immunologically and genetical characterized as the N protein of a novel hantavirus associated with ARDS cases in the Four Corners area of the United States. Use of the recombinant N protein in immunological assays, especially ELISA, improved the specificty and sensitivity of those assays compared to heterologous antigens used so far in diagnosis. The presented data clearly demonstrate that the *E. coli* expressed N protein is a potent antigen for diagnostic assays and the higher specificity can result in an earlier detection of infected cases.

TABLE 1

| Serum/serotype | | Immunoblot[a] *E. coli*/VVT7[c] | RIP[b] VVT7[f] | IFA[e] VVT7[g] | ELISA[d] *E. coli*[h] IgM/IgG | |
|---|---|---|---|---|---|---|
| NE1 | PUU | + | + | + | 40 | — | 400 |
| NE2 | PUU | + | + | + | 320 | 6400 | 1600 |
| KHF1 | HTN | − | − | − | − | − | − |
| KHF2 | HTN | − | − | − | − | − | − |
| A | FCV | +++ | +++ | ++ | >640 | 6400 | 6400 |
| B | FCV | +++ | +++ | +++ | 320 | − | 6400 |
| C | FCV | ++ | + | + | 80 | 100 | − |
| D | FCV | +++ | ++ | − | 80 | 6400 | 1600 |
| E | FCV | +++ | ++ | − | >640 | 6400 | 400 |
| F | — | − | − | − | − | − | − |
| G | — | − | − | − | − | − | − |
| H | — | − | − | − | − | − | − |
| I | — | − | − | − | − | − | − |
| J | — | − | − | − | − | − | − |
| rabbit | SEO | ++ | + | n.d. | 80 | n.d. | 1600 |
| rabbit | HITN | + | + | n.d. | − | n.d. | 400 |
| rabbit | PUU | ++ | + | n.d. | 40 | n.d. | 6400 |
| rabbit | PHV | ++ | + | n.d. | 80 | n.d. | 6400 |

[a]All sera were used in a dilution of 1:250.
[b]All sera were used in a dilution of 1:40.
[c]All sera were used in a serial dilution of 1:2 beginning with 1:20.
[d]All sera were used in a serial dilution of 1:2 beginning with 1:100.
[e]Ni-purified N protein expressed in *E. coli* and cell lysates infected with VVT7 and transfected with pTM1-Nfc were separated on 10% SDS-PAGE, blotted onto nitrocellulose, and used for the immuno assay.
[f]Total cell lysate of VVt7-infected and pTM1-Nfc transfected Hela cells were used in the immunoprecipitation assay.
[g]VVT7-infected and pTM1-Nfc transfected Hela cells were used for the IFA.
[h]Ni-purified N protein express in *E. coli* was used to coat ELISA plates.

Throughout this application, various publications are referenced. The disclosures of these publications in their entireties are hereby incorporated by reference into this application in order to more fully describe the state of the art to which this invention pertains.

Although the present process has been described with reference to specific details of certain embodiments thereof, it is not intended that such details should be regarded as limitations upon the scope of the invention except as and to the extent that they are included in the accompanying claims.

What is claimed is:

1. A method of detecting the presence of a Hantavirus of the type designated Four Corners Virus in a sample, comprising reverse transcribing viral RNA in the sample to DNA followed by amplification of the DNA using a primer having a nucleotide sequence set forth in the Sequence Listing as SEQ ID NO:8 and detecting the presence of an amplification product, whereby the presence of the amplification product is correlated with the presence of the Hantavirus in the sample.

2. A method of detecting the presence of a Hantavirus of the type designated Four Corners Virus in a sample, comprising reverse transcribing viral RNA in the sample to DNA followed by amplification of the DNA using a primer having a nucleotide sequence set forth in the Sequence Listing as SEQ ID NO:9 and detecting the presence of an amplification product, whereby the presence of the amplification product is correlated with the presence of the Hantavirus in the sample.

3. A method of detecting the presence of a Hantavirus of the type designated Four Corners Virus in a sample, comprising reverse transcribing viral RNA in the sample to DNA followed by amplification of the DNA using primer having a nucleotide sequence set forth in the Sequence Listing as SEQ ID NO:10 and detecting the presence of an amplification product, whereby the presence of the amplification product is correlated with the presence of the Hantavirus in the sample.

4. A method of detecting the presence of a Hantavirus of the type designated Four Corners Virus in a sample, comprising reverse transcribing viral RNA in the sample to DNA followed by amplification of the DNA using a primer having a nucleotide sequence set forth in the Sequence Listing as SEQ ID NO:11 and detecting the presence of an amplification product, whereby the presence of the amplification product is correlated with the presence of the Hantavirus in the sample.

5. A method of detecting the presence of a Hantavirus of the type designated Four Corners Virus in a sample, comprising reverse transcribing viral RNA in the sample to DNA followed by amplification of the DNA using a primer having a nucleotide sequence which hybridizes to a nucleotide sequence set forth in the Sequence Listing as SEQ ID NO:1, SEQ ID NO:2, SEQ ID NO:3, SEQ ID NO:4 or SEQ ID NO:5, or to a nucleotide sequence complementary to a nucleotide sequence set forth in the Sequence Listing as SEQ ID NO:1, SEQ ID NO:2, SEQ ID NO:3, SEQ ID NO:4 or SEQ ID NO:5, and which does not hybridize to nucleotide sequences present in Hantaan, Seoul, Puumala or Prosect Hill Hantaviruses, and detecting the presence of an amplification product, whereby the presence of the amplification product is correlated with the presence of the Hantavirus in the sample.

6. An isolated virus of the type designated Four Corners Virus, comprising a ribonucleic acid sequence fully complementary to nucleotide sequences set forth in the Sequence Listing as SEQ ID NO:1 and SEQ ID NO:2.

7. A nucleic acid comprising an isolated or purified RNA having a nucleotide sequence fully complementary to a nucleotide sequence set forth in the Sequence Listing as SEQ ID NO:1 or a purified DNA having a nucleotide sequence set forth in the Sequence Listing as SEQ ID NO:1.

8. A vector comprising the nucleic acid of claim 7.

9. A nucleic acid comprising an isolated or purified RNA having a nucleotide sequence fully complementary to a nucleotide sequence set forth in the Sequence Listing as SEQ ID NO:2 or a purified DNA having a nucleotide sequence set forth in the Sequence Listing as SEQ ID NO:2.

10. A vector comprising the nucleic acid of claim 9.

11. A nucleic acid comprising an isolated or purified RNA having a nucleotide sequence fully complementary to a nucleotide sequence set forth in the Sequence Listing as SEQ ID NO:3 or a purified DNA having a nucleotide sequence set forth in the Sequence Listing as SEQ ID NO:3.

12. A vector comprising the nucleic acid of claim 11.

13. A nucleic acid comprising an isolated or purified RNA having a nucleotide sequence fully complementary to a nucleotide sequence set forth in the Sequence Listing as SEQ ID NO:4 or a purified DNA having a nucleotide sequence set forth in the Sequence Listing as SEQ ID NO:4.

14. A vector comprising the nucleic acid of claim 13.

15. A nucleic acid comprising an isolated or purified RNA having a nucleotide sequence fully complementary to a nucleotide sequence set forth in the Sequence Listing as SEQ ID NO:5 or a purified DNA having a nucleotide sequence set forth in the Sequence Listing as SEQ ID NO:5.

16. A vector comprising the nucleic acid of claim 15.

17. An oligonuclcotide primer selected from the group consisting of the sequence set forth in the Sequence Listings as SEQ ID NO:8; SEQ ID NO:9; SEQ ID NO: 10 and SEQ ID NO: 11.

\* \* \* \* \*